United States Patent
Selvaraj et al.

(10) Patent No.: US 11,357,769 B2
(45) Date of Patent: Jun. 14, 2022

(54) DRUG COMBINATIONS FOR REDUCING CELL VIABILITY AND/OR CELL PROLIFERATION

(71) Applicant: Eisai R&D Management Co., Ltd., Tokyo (JP)

(72) Inventors: Anand Selvaraj, Cambridge, MA (US); Peter Smith, Arlington, MA (US)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

(21) Appl. No.: 16/300,313

(22) PCT Filed: May 9, 2017

(86) PCT No.: PCT/US2017/031771
§ 371 (c)(1),
(2) Date: Nov. 9, 2018

(87) PCT Pub. No.: WO2017/196854
PCT Pub. Date: Nov. 16, 2017

(65) Prior Publication Data
US 2019/0117640 A1    Apr. 25, 2019

Related U.S. Application Data

(60) Provisional application No. 62/334,102, filed on May 10, 2016.

(51) Int. Cl.
*A61K 31/497* (2006.01)
*A61K 31/535* (2006.01)
(Continued)

(52) U.S. Cl.
CPC ........ *A61K 31/4706* (2013.01); *A61K 31/506* (2013.01); *A61K 31/517* (2013.01); *A61P 35/00* (2018.01); *A61K 39/3955* (2013.01)

(58) Field of Classification Search
CPC .............. A61K 31/506; A61K 31/5377; A61K 31/517; A61K 39/3955
(Continued)

(56) References Cited

U.S. PATENT DOCUMENTS

| | | |
|---|---|---|
| 7,371,750 B2 | 5/2008 | Sim et al. |
| 7,501,425 B1 | 3/2009 | Dobrusin et al. |

(Continued)

FOREIGN PATENT DOCUMENTS

| | | |
|---|---|---|
| WO | 2006000420 A1 | 1/2006 |
| WO | 2006038112 A1 | 4/2006 |

(Continued)

OTHER PUBLICATIONS

Ho et al. "Fibroblast growth factor receptor 4 regulates proliferation, anti-apoptosis and alpha-fetoprotein secretion during hepatocellular carcinoma progression and represents a potential target for therapeutic intervention," J. Heptology, 2009, vol. 50, pp. 118-127. (Year: 2009).*

(Continued)

*Primary Examiner* — Shengjun Wang
(74) *Attorney, Agent, or Firm* — Buchanan Ingersoll & Rooney PC

(57) ABSTRACT

Provided herein is a combination of agents for reducing cell viability and/or cell proliferation. The combination comprises an FGFR4 inhibitor and an EGFR inhibitor.

29 Claims, 10 Drawing Sheets

DOSE MATRIX

Vertical axis is Gefitinib (μM).
Horizontal axis is Compound 1 (μM).

(51) Int. Cl.

| | |
|---|---|
| A61K 31/4706 | (2006.01) |
| A61K 31/506 | (2006.01) |
| A61K 31/517 | (2006.01) |
| A61P 35/00 | (2006.01) |
| A61K 39/395 | (2006.01) |

(58) Field of Classification Search
USPC .......................................... 514/252.14, 234.5
See application file for complete search history.

(56) References Cited

U.S. PATENT DOCUMENTS

| | | | |
|---|---|---|---|
| 8,552,002 | B2 | 10/2013 | Ding et al. |
| 9,434,697 | B2 | 9/2016 | Reynolds et al. |
| 9,730,931 | B2 | 8/2017 | Reynolds et al. |
| 2010/0120773 | A1 | 5/2010 | Guagnano et al. |
| 2010/0143386 | A1 | 6/2010 | Ullrich et al. |
| 2010/0189775 | A1* | 7/2010 | Bolondi ............... A61K 31/704 424/450 |
| 2011/0179505 | A1 | 7/2011 | Ullrich et al. |
| 2013/0040949 | A1 | 2/2013 | Gray et al. |
| 2013/0137708 | A1 | 5/2013 | Garske et al. |
| 2013/0183294 | A1 | 7/2013 | Pai et al. |
| 2014/0088100 | A1 | 3/2014 | Bifulco et al. |
| 2014/0142084 | A1 | 5/2014 | Kameda et al. |
| 2014/0296216 | A1 | 10/2014 | Ding et al. |
| 2016/0130237 | A1 | 5/2016 | Reynolds et al. |
| 2017/0007601 | A1 | 1/2017 | Reynolds et al. |
| 2017/0360785 | A1 | 12/2017 | Reynolds et al. |
| 2018/0093972 | A1 | 4/2018 | Moniz et al. |

FOREIGN PATENT DOCUMENTS

| | | |
|---|---|---|
| WO | 2007071752 A2 | 6/2007 |
| WO | 2009158571 | 12/2009 |
| WO | 2011071821 A1 | 6/2011 |
| WO | 2011088196 A2 | 7/2011 |
| WO | 2012136732 A1 | 10/2012 |
| WO | 2012167415 A1 | 12/2012 |
| WO | 2014011900 A2 | 1/2014 |
| WO | 2014144737 A1 | 9/2014 |
| WO | 2014149164 A1 | 9/2014 |
| WO | 20150006492 A1 | 1/2015 |
| WO | 2015030021 A1 | 3/2015 |
| WO | 2015057938 A1 | 4/2015 |
| WO | 2015057963 A1 | 4/2015 |
| WO | 2015061572 A1 | 4/2015 |
| WO | 2015108992 A1 | 7/2015 |
| WO | 2016168331 A1 | 10/2016 |
| WO | 2017198149 A1 | 11/2017 |
| WO | 2017198221 A1 | 11/2017 |

OTHER PUBLICATIONS

Hu et al. ("Recent advances of cocktail chemotherapy by combination drug delivery systems," Advanced Drug Delivery Reviews, 2016, vol. 98, pp. 19-34). (Year: 2016).*
International Search Report (PCT/ISA/210) dated Feb. 3, 2015, by the European Patent Office as the International Searching Authority for International Application No. PCT/US2014/060857.
Written Opinion (PCT/ISA/237) dated Feb. 3, 2015, by the European Patent Office as the International Searching Authority for International Application No. PCT/US2014/060857.
Guagnano et al., "Discovery of 3-(2.6-Dichloro-3.5-dimethoxyphenyl)-1-{6-[4-(4-ethyl-piperazin-1-yl)-phenylamino]pyrimidin-4-yl}-1-methyl-urea(NVP-BGJ398). A Potent and Selective Inhibitor of the Fibroblast Growth Factor Receptor Family of Receptor Tyrosine Kinase", Journal of Medicinal Chemistry, Oct. 2011, pp. 7066-7083, vol. 54, No. 2.
Liew et al., "SVM Model for Virtual Screening of Lck Inhibitors", J. Chem. Inf. Model., 2009, pp. 877-885, vol. 49, No. 4.
Maier et al., "Development of N-4,6-pyrimidme-N-alkyl-N0-phenyl ureas as orally active inhibitors of lymphocyte specific tyrosine kinase", Bioorganic & Medicinal Chemistry Letters, 2006, pp. 3646-3650, vol. 16.
Anwer et al., "A QSAR Study on Some Series of Anticancer Tyrosine Kinase Inhibitors", Medicinal Chemistry, 2013, pp. 203-212, vol. 9, No. 2.
Tan et al., "Development of covalent inhibitors that can overcome resistance to first-generation FGFR kinase inhibitors", PNAS, Oct. 2014, pp. E4869-E4877.
Zhang et al., "Targeting cancer with small molecule kinase inhibitors", Nature Reviews/Cancer, Jan. 2009, pp. 28-39, vol. 9 (including one page of Supplementary Information).
Anastassiadis et al., "Comprehensive assay of kinase catalytic activity reveals features of kinase inhibitor selectivity", Nature Biotechnology, Nov. 2011, pp. 1039-1046, vol. 29, No. 11.
Brooks et al., "Molecular Pathways: Fibroblast growth factor signaling: a new therapeutic opportunity in cancer", Clinical Cancer Research, Mar. 2012, pp. 1-25.
Dieci et al., "Fibroblast Growth Factor Receptor Inhibitors as a Cancer Treatment: From a Biologic Rationale to Medical Perspectives", Cancer Discovery, Feb. 2013, pp. OF1-OF16.
French et al., "Targeting FGFR4 Inhibits Hepatocellular Carcinoma Preclinical Mouse Models", PLoS ONE, May 2012, pp. 1-12, vol. 7, issue 5.
Liu et al., "Developing Irreversible Inhibitors of the Protein Kinase Cysteinome", Chemistry & Biology Review, Feb. 2013, pp. 146-159, vol. 20.
Gavine et al., "AZD4547: An Orally Bioavailable, Potent, and Selective Inhibitor of the Fibroblast Growth Factor Receptor Tyrosine Kinase Family", Cancer Research, Feb. 2012, pp. 2045-2056, vol. 72, No. 8.
Olechno et al., "Improving IC50 Results with Acoustic Droplet Ejection", Technical Brief JALA, Aug. 2006, pp. 240-246.
Pelaez-Garcia et al., "FGFR4 Role in Epithelial-Mesenchymal Transition and Its Therapeutic Value in Colorectal Cancer", PLOS One, May 2013, pp. 1-11, vol. 8, issue 5.
Santos et al., "Michael Acceptors as Cysteine Protease Inhibitors", Mini-Reviews in Medicinal Chemistry, 2007, pp. 1040-1050, vol. 7, No. 10.
Sawey et al., "Identification of a Therapeutic Strategy Targeting Amplified FGF19 in Liver Cancer by Oncogenomic Screening", Cancer Cell, pp. 347-358, Mar. 2011, vol. 19.
Wesche et al., "Fibroblast growth factors and their receptors in cancer", Biochem. Journal, 2011, pp. 199-213.
Yanochko et al., "Pan-FGFR Inhibition Leads to Blockade of FGF23 Signaling, Soft Tissue Mineralization, and Cardiovascular Dysfunction", Toxicological Sciences, Jul. 2013, pp. 1-14.
Zaid et al., "Identification of FGFR4 as a Potential Therapeutic Target for Advanced-Stage, High-Grade Serous Ovarian Cancer", Clinical Cancer Research, Jan. 2013, pp. 809-820, vol. 19, No. 4.
Zhao et al., "A Novel, Selective Inhibitor of Fibroblast Growth Factor Receptors That Shows a Potent Broad Spectrum of Antitumor Activity in Several Tumor Xenograft Models", Molecular Cancer Therapeutics, Sep. 2011, pp. 2200-2210, vol. 10, No. 11.
Hagel et al., "First Selective Small Molecule Inhibitor of FGFR4 for the Treatment of Hepatocellular Carcinomas with an Activated FGFR4 Signaling Pathway", American Association for Cancer Research Journal, Mar. 2015, pp. 1-26.
Xu et al., "FGFR4 Gly388Arg polymorphism contributes to prostate cancer development and progression: A meta-analysis of 2618 cases and 2305 controls", BMC Cancer, 2011, pp. 1-6.
Miura et al., "Fibroblast growth factor 19 expression correlates with tumor progression and poorer prognosis of hepatocellular carcinoma", BMC Cancer, 2012, pp. 1-15.
Boyd et al., "Data Display and Analysis Strategies for the NCI Disease-Oriented in Vitro Antitumor Drug Screen", Cytotoxic Anticancer Drugs: Models and Concepts for Drug Discovery and Development, 1992, pp. 11-34.
Streit et al., "FGFR4 Arg388 allele correlates with tumour thickness and FGFR4 protein expression with survival of melanoma patients", British Journal of Cancer, 1994, pp. 1879-1886, vol. 94, No. 12.

(56) References Cited

OTHER PUBLICATIONS

Ye et al., "Fibroblast Growth Factor Receptor 4 Regulates Proliferation and Antiapoptosis During Gastric Cancer Progression", Cancer, Dec. 2011, pp. 5304-5313.
Chiang et al., "Focal Gains of VEGFA and Molecular Classification of Hepatocellular Carcinoma", American Association for Cancer Research Journal, Aug. 2008, pp. 6779-6788.
Sia et al., "Integrative Molecular Analysis of Intrahepatic Cholangiocarcinoma Reveals 2 Classes That Have Different Outcomes", Gastroenterology, 2013, pp. 829-840, vol. 144, No. 4.
Motoda et al., "Overexpression of fibroblast growth factor receptor 4 in high-grade pancreatic intraepithelial neoplasia and pancreatic ductal adenocarcinoma", International Journal of Oncology, 2011, pp. 133-143, vol. 38.
Taylor Vi et al., "Identification of FGFR4-activating mutations in human rhabdomyosarcomas that promote metastasis in xenotransplanted models", The Journal of Clinical Investigation, Nov. 2009, pp. 3395-3407, vol. 119, No. 11.
Monks et al., "Feasibility of a High-Flux Anticancer Drug Screen Using a Diverse Panel of Cultured Human Tumor Cell Lines", Articles, Jun. 1991, pp. 757-766, vol. 83, No. 11.
Berge et al., "Pharmaceutical Salts", Journal of Pharmaceutical Sciences, Jan. 1977, pp. 1-19, vol. 66, No. 1.
Barderas et al., "An optimized predictor panel for colorectal cancer diagnosis based on the combination of tumor-associated antigens obtained from protein and phage microarrays", Journal of Proteomics, 2012, pp. 4647-4655, vol. 75.
Fawdar et al., "Targeted genetic dependency screen facilitates identification of actionable mutations in FGFR4, MAP3K9, and PAK5 in lung cancer", PNAS, Jul. 2013, pp. 12426-12431, vol. 110, No. 30.
Office Action dated Apr. 18, 2017, in Chinese Application No. 201480056358.4.
Office Action dated Sep. 20, 2017, in Colombian Application No. 16097757.
Lima, et al., "Bioisosterism: A Useful Strategy for Molecular Modification and Drug Design", Current Medicinal Chem., 2005, pp. 23-49, vol. 12.
International Search Report (PCT/ISA/210) dated Jun. 10, 2016, by the European Patent Office as the International Searching Authority for International Application No. PCT/US2016/027334.
Written Opinion (PCT/ISA/237) dated Jun. 10, 2016, by the European Patent Office as the International Searching Authority for International Application No. PCT/US2016/027334.
S. Datta et al., 3 Nature Reviews / Drug Discovery, 42-57 (2004).
International Search Report (PCT/ISA/210) dated Jul. 13, 2017, by the European Patent Office as the Internationa Searching Authority for International Application No. PCT/US2017/031771.
Written Opinion (PCT/ISA/237) dated Jul. 13, 2017, by the European Patent Office as the International Searching Authority for International Application No. PCT/US2017/031771.
Fuchs et al., "Epithelial-to-Mesenchymal Transition and Integrin-Linked Kinase Mediate Sensitivity to Epidermal Growth Factor Receptor Inhibition in Human Hepatoma Cells", Cancer Research, Apr. 1, 2008, vol. 68, No. 7, pp. 2391-2399.
Asnacios et al. "Gemcitabine Plus Oxaliplatin (GEMOX) Combined With Cetuximab in Patients With Progressive Advanced Stage Hepatocellular Carcinoma", Cancer, Jun. 15, 2008, vol. 112, No. 12, pp. 2733-2739.
Office Action dated Apr. 13, 2021, in Corresponding Japanese Application No. 2018-559826, with English Translation.
Smith, et al., "Synergistic and Additive Combinations of Several Antitumor Drugs and Other Agents with the Potent Alkylating Agent Adozelesin," Cancer Chemo. & Pharm., 35, 471-482 (1995).
Distefano, et al., "Antagonistic Effect of the Combination Gemcitabine/Topotecan in Ovarian Cancer Cells," Oncol. Res. 12(9-10);355-9 (2001).
Jessie Peh, et al., "The combination of vemurafenib and procaspase-3 activation is synergistic in mutant BRAF melanomas" HHS Public Access, Mol Cancer Ther. Aug. 2016; 15(8): 1859-1869. doi:10. 1158/1535-7163. MCT-16-0025.
Jing Tang, et al., "What is Synergy? The Saariselka agreement revisited", Frontiers in Pharmacology, published Sep. 1, 2015.
Remzi Celebi, et al., "In-silico Prediction of Synergistic Anti-Cancer Drug Combinations Using Multi-omics Data", Scientific Reports, (2019) 9:8949, https://doi.org/10.1038/s41598-019-45236-6.
Andrew X. Zhu, et al., "Search: A Phase III, Randomized, Double-Blind, Placebo-Controlled Trial of Sorafenib Plus Erlotinib in Patients With Advanced Hepatocellular Carcinoma", Journal of Clinical Oncology, vol. 33, No. 6, Feb. 20, 2015, Downloaded from ascopubs.org by Crai Universitat De Barcelona on Nov. 6, 2017 from 161.116.100.134 Copyright © 2017 American Society of Clinical Oncology.
Marco Le Grazie, et al., "Chemotherapy for hepatocellular carcinoma: The present and the future", http://www.f6publishing.com DOI: 10.4254/wjh.v9.i21.907; World J Hepatol Jul. 28, 2017; 9(21): 907-920 ISSN 1948-5182 (online).

\* cited by examiner

DOSE MATRIX

Vertical axis is Gefitinib (μM).
Horizontal axis is Compound 1 (μM).

Loewe Excess over Additivity

Vertical axis is Gefitinib (μM).
Horizontal axis is Compound 1 (μM).

Vertical axis is Afatinib (μM).
Horizontal axis is Compound 1 (μM).

Loewe Excess over Additivity

Verticle axis is Afatinib (uM).
Horizontal axis is Compound 1 (uM).

Verticle axis is Lapatinib (uM).
Horizontal axis is Compound 1 (uM).

Verticle axis is Lapatinib (uM).
Horizontal axis is Compound 1 (uM).

Dose Matrix / HEP3B.2

Vertical axis is Compound 1 (μM).
Horizontal axis is Cetuximab (μM).

Vertical axis is Compound 1 (μM).
Horizontal axis is Cetuximab (μM).

DRUG COMBINATIONS FOR REDUCING CELL VIABILITY AND/OR CELL PROLIFERATION

CROSS-REFERENCE TO RELATED APPLICATIONS

This application claims the benefit of U.S. Provisional Patent Application No. 62/334,102, filed on May 10, 2016. That application is incorporated by reference herein.

BACKGROUND

Liver cancer is the second greatest cause of mortality from any type of cancer, and the 16th most common cause of death worldwide (Llovet J M, et al., 2015 "Advances in targeted therapies for hepatocellular carcinoma in the genomic era." *Nat. Rev. Clin Oncology* 12, 408-424). Hepatocellular carcinoma (HCC) accounts for up to 90% of all primary liver cancers (Llovet J M et al. 2015).

Various signaling pathways have been implicated in HCC, including fibroblast growth factors (FGF) (particularly FGF19/FGFR4), epidermal growth factor (EGF), vascular endothelial growth factor (VEGF), ERK/MAPK, and mechanistic target of rapamycin (mTOR), among others (Llovet J M et al., 2015). FGF19 is overexpressed in about a third of all HCC, and this overexpression is hypothesized to hyperactivate FGFR4 and its downstream signaling pathway leading to enhanced tumor growth (Xie M H et al., 1999 "FGF-19, a novel fibroblast growth factor with unique specificity for FGFR4." *Cytokine*. 1999 October; 11(10): 729-35; Sawey, et al., 2011 "Identification of a therapeutic strategy targeting amplified FGF19 in liver cancer by Oncogenomic screening." *Cancer Cell*. 2011 Mar. 8; 19(3): 347-58.). Similar to FGF19/FGFR4 pathway, EGFR is also overexpressed in 40-70% of HCC, and its activation is involved in HCC pathogenesis (Chua C W L et al., 2011. Targeted Therapy in Hepatocellular Carcinoma. *Int J Hepatol*. 2011; 2011: 348297).

Compound 1 is a selective, orally bioavailable small molecule FGFR4 inhibitor with the structure shown in Formula I, and the chemical name N-(2-((6-(3-(2,6-dichloro-3,5-dimethoxyphenyl)-1-methylureido)pyrimidin-4-yl)amino)-5-(4-ethylpiperazin-1-yl)phenyl)acrylamide:

(I)

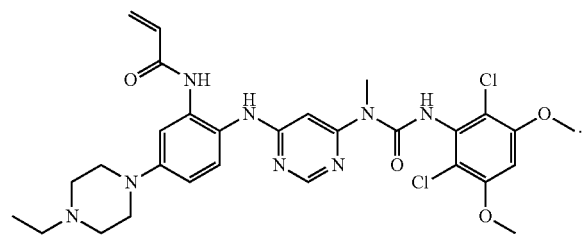

Compound 1 and its synthesis are reported in PCT International Application Publication No. WO2015/057938, published on Apr. 23, 2015. That document is incorporated by reference herein.

Gefitinib (4-quinazolinamine N-(3-chloro-4-fluorophenyl)-7-methoxy-6-[3-(4-morpholinyl)propoxy])) is an FDA-approved EGFR inhibitor. Gefitinib is a free base with the following structure:

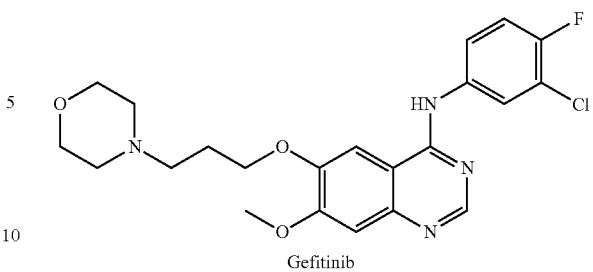

Gefitinib

See U.S. Pat. No. 5,770,599, which is incorporated by reference herein.

Afatinib (2-butenamide, N-[4-[(3-chloro-4-fluorophenyl)amino]-7-[[(3S)-tetrahydro-3-furanyl]oxy]-6-quinazolinyl]-4-(dimethylamino)-,(2E)-, (2Z)-2-butenedioate (1:2) is an FDA-approved EGFR inhibitor. Afatinib is typically administered as a dimaleate salt, and has the following structure:

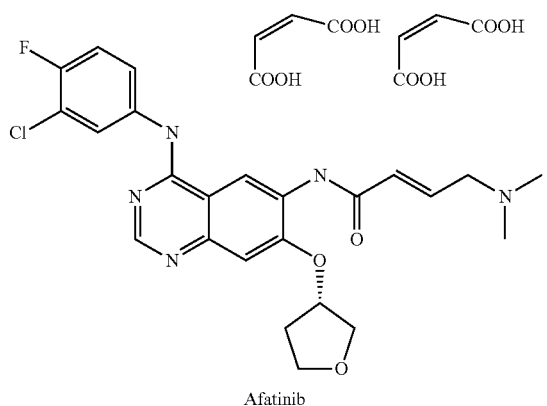 [SMILES: CN(C)C/C=C/C(=O)Nc1cc2c(Nc3ccc(F)c(Cl)c3)ncnc2cc1O[C@H]1CCOC1 ; O=C(O)/C=C\C(=O)O ; O=C(O)/C=C\C(=O)O]

Afatinib

See U.S. Pat. Nos. 6,251,912; 8,426586; 8,545,884; and RE43431, all of which are incorporated by reference herein.

Lapatinib (N-(3-chloro-4-{[(3-fluorophenyl)methyl]oxy}phenyl)-6-[5-({[2-(methylsulfonyl)ethyl]amino}methyl)-2-furanyl]-4-quinazolinamine bis(4-methylbenzenesulfonate) monohydrate) is an FDA-approved EGFR inhibitor. Lapatinib is typically administered as a ditosylate monohydrate with the following formula:

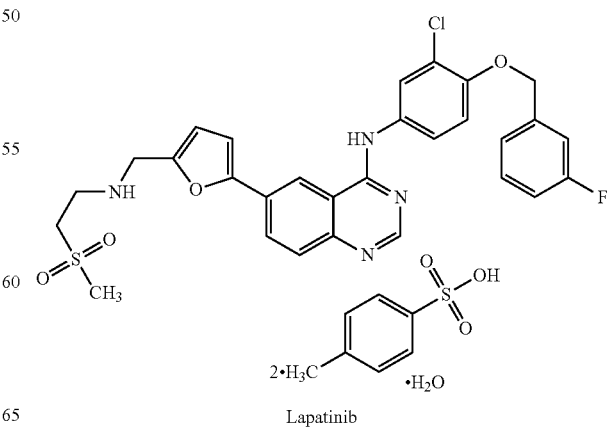

Lapatinib

See International Patent Application PCT/EP99/00048, published as WO 99/35146 and PCT/US01/20706, published as WO 02/02552, both of which are incorporated by reference herein.

Cetuximab is an FDA-approved inhibitor of the EGFR receptor. Cetuximab is a chimeric (mouse/human) monoclonal antibody binds specifically to the extracellular domain of the human EGFR. Cetuximab is reported, for example, in U.S. Pat. No. 6,217,866, which is incorporated by reference herein.

Despite advances in the treatment of HCC, there is a need to provide improved treatment for HCC.

SUMMARY

Embodiments provide a combination of Compound 1 and an EGRF inhibitor for reducing the viability and/or proliferation of one or more cells. In certain embodiments the EGFR inhibitor is gefitinib. In other embodiments the EGFR inhibitor is afatinib. In still other embodiments the EGFR inhibitor is lapatinib. In yet other embodiments the EGFR inhibitor is cetuximab. Use of the combination of Compound 1 and an EGRF inhibitor may lead to a synergistic reduction in the viability and/or proliferation of the cells. In certain embodiments the cells are hepatocellular cells. In certain embodiments the reduction in the viability and/or proliferation of the cells is an in vitro reduction.

Embodiments may provide a combination therapy, comprising an effective amount of Compound 1 and an effective amount of an EGFR inhibitor. In certain embodiments the EGFR inhibitor is gefitinib. In other embodiments the EGFR inhibitor is afatinib. In still other embodiments the EGFR inhibitor is lapatinib. Combination therapy provided herein may lead to a synergistic reduction in the viability of HCC cells and may lead to tumor growth inhibition of HCC in patients in need of treatment.

Embodiments may provide a method of reducing cell viability or cell proliferation, comprising administering to one or more cells a combination of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor or a pharmaceutically acceptable salt thereof.

Embodiments may provide a method of treating hepatocellular carcinoma in a patient in need thereof, including administering to the patient combination of N-(2-((6-(3-(2, 6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor or a pharmaceutically acceptable salt thereof. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 50 mg to 600 mg. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 200 mg to 400 mg. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage of 300 mg.

In some embodiments the EGFR inhibitor is selected from, for example, 4-quinazolinamine N-(3-chloro-4-fluorophenyl)-7-methoxy-6-[3-(4-morpholinyl)propoxy]) (gefitinib), N-[4-[(3-Chloro-4-fluorophenyl)amino]-7-[[(3S)-tetrahydro-3-furanyl]oxy]-6-quinazolinyl]-4(dimethylamino)-2-butenamide) (afatinib), and N-(3-chloro-4-{[(3-fluorophenyl)methyl]oxy}phenyl)-6-[5-({[2-(methylsulfonyl)ethyl]amino}methyl)-2-furanyl]-4-quinazolinamine bis(4-methylbenzenesulfonate) monohydrate (lapatinib).

In some embodiments the EGFR inhibitor is gefitinib. Gefitinib may be administered, for example in a daily dosage of 250 mg.

In some embodiments the EGFR inhibitor is afatinib. Afatinib may be administered, for example, in a daily dosage of 20 mg/day. Afatinib may be administered, for example, in a daily dosage of 30 mg/day. Afatinib may be administered, for example, in a daily dosage of 40 mg/day.

In some embodiments the EGFR inhibitor is lapatinib. Lapatinib may be administered, for example, in a daily dosage of between 1000 mg to 1500 mg. Lapatinib may be administered, for example, in a daily dosage of 1000 mg. Lapatinib may be administered, for example, in a daily dosage of 1250 mg. Lapatinib may be administered, for example, in a daily dosage of 1500 mg.

In some embodiments the EGFR inhibitor is cetuximab. Cetuximab is commercially available as ERBITUX® from Eli Lilly and Company and its affiliates, which provide it as 100 mg/50 ml and 200 mg/100 ml vials. Cetuximab is typically administered by injection for intravenous infusion. Dosage of cetuximab typically involves premedication with an $H_1$ antagonist, followed by administration of a 400 mg/m2 initial dose as a 120-minute intravenous infusion followed by 250 mg/m2 weekly infused over 60 minutes. In some embodiments the infusion rate is reduced by 50% if an infusion reaction should occur.

In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered as separate formulations in any order. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered as a single formulation. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered sequentially. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered simultaneously.

In some embodiments the form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide that is administered is the free base form. In some embodiments the form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide that is administered is a hydrochloride salt form.

Further embodiments may provide a pharmaceutical formulation including N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor or a pharmaceutically acceptable salt thereof. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a free base form. In some embodiments the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a hydrochloride salt form.

Further embodiments may provide use of a combination of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor in the treatment of hepatocellular carcinoma. Further embodiments may provide use of a combination of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor in the preparation of a medicament for treatment of hepatocellular carcinoma.

DETAILED DESCRIPTION OF EMBODIMENTS

Figure 1A:
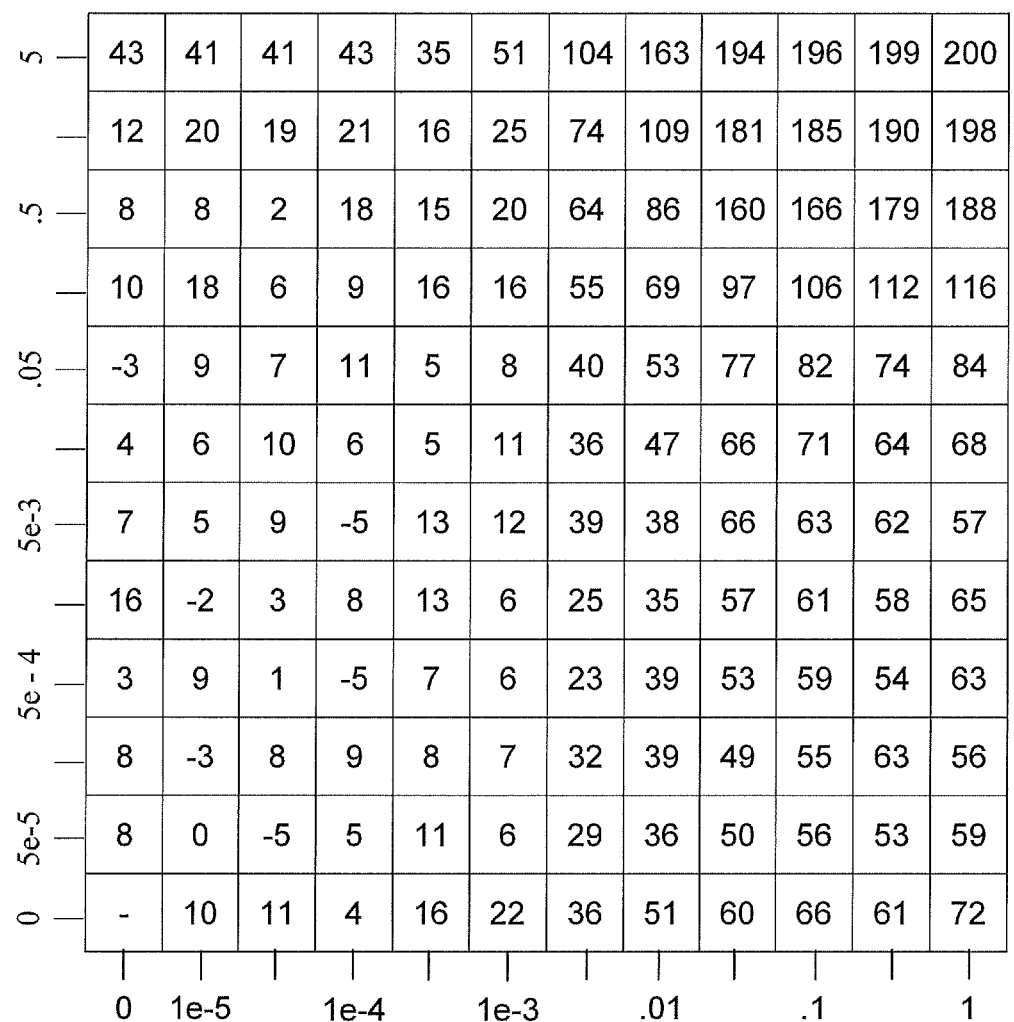
FIG. 1A shows inhibition of cell viability as measured by CellTiter-Glo for Compound 1 and gefitinib.

Provided herein are combinations of Compound 1 and an EGFR inhibitor for reducing cell viability and or cell proliferation. In certain embodiments the EGFR inhibitor is gefitinib. In other embodiments, the EGFR inhibitor is afatinib. In still other embodiments, the EGFR inhibitor is lapatinib. In still other embodiments, the EGFR inhibitor is cetuximab. Such combinations may lead to a synergistic reduction in cell viability and/or cell proliferation. In certain embodiments the reduction in cell viability and/or cell proliferation is an in vitro reduction.

Provided herein are therapies useful in reducing the viability or proliferation of one or more cells. Such therapies may be useful for treating hepatocellular carcinoma (HCC) and intrahepatic cholangiocarcinoma (IHCC). In some embodiments, the combination therapies include administration of Compound 1 in combination with an EGFR inhibitor. In certain embodiments the EGFR inhibitor is gefitinib. In other embodiments, the EGFR inhibitor is afatinib. In still other embodiments, the EGFR inhibitor is lapatinib.

Provided herein are combinations of therapeutic agents and methods for administration of the combination of agents that may be useful to treat hepatocellular carcinoma. As used herein, a "combination of therapeutic agents" and similar terms refer to a combination of two types of therapeutic agents: (1) Compound 1 and/or pharmacologically active salts thereof and (2) an EGFR inhibitor, and/or pharmacologically active salts thereof. "Combination" as used herein (including in the term "combination of therapeutic agents") refers to these types of therapeutic agents co-formulated in a single dosage form, individually formulated and co-administered, or individually formulated and sequentially administered.

Compound 1 is a selective, orally bioavailable small molecule FGFR4 inhibitor with the structure shown in Formula I:

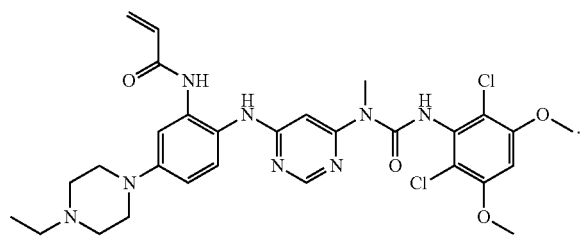

(I)

Compound 1 and its synthesis are reported in PCT International Application Publication No. WO2015/057938, published on Apr. 23, 2015. That document is incorporated by reference herein. Compound 1 may also be used alone or in combinations described herein as treatment for HCC or cholangiocarcinoma, including intrahepatic cholangiocarcinoma (IHCC). When used alone or in combinations as described herein, Compound 1 may be administered to patients in any of the following daily dosage amounts: 150 mg, 300 mg, 600 mg, 1000 mg, 1500 mg or 2000 mg. The daily dosage amount may be from 50 mg to 3000 mg, from 50 mg to 600 mg, or from 200 mg to 400 mg. The daily dosage may be part of a cyclic regimen lasting 14 days or 21 days. The daily dosage amount may be administered as a single dosage or as multiple dosages.

EGFR inhibitors suitable for use herein may include neutralizing monoclonal antibodies, including for example cetuximab, which is an immunoglobulin G1 human-murine chimeric counterpart of the murine monoclonal antibody M225; and panitumumab, which is a fully human IgG2 targeting the extracellular domains of EGFR monoclonal antibody, as reported in Martinelli, E, et al., 2009 "Anti-epidermal Growth Factor Receptor Monoclonal Antibodies in Cancer Therapy." Clin. Exper. Immuno. 158: 1-9, which is incorporated by reference herein. EGFR inhibitors may further include tyrosine kinase inhibitors, including for example gefitinib, erlotinib, lapatinib, icotinib, KD019, varlitinib, BMS599626, JNJ26483327, TAK285, AL6802, PKI166, AEE788, afatinib, dacomitinib, neratinib, poziotinib, BMS690514, CUDC101, KKI357, AV412, canertinib, pelitinib, WZ4002, CO-1686, AZD-9291, HM61713, and TAS-2913. See, for example, Lee, C, et al., 2014 "Small-molecule EGFR Tyrosine Kinase Inhibitors for the Treatment of Cancer." Expert Opin. Investig. Drugs 23(10): 1333-1348, which is incorporated by reference herein.

Administration of a combination of therapeutic agents may comprise administration of the individual therapeutic agents in combination in a single formulation or unit dosage form, administration of the individual therapeutic agents of the combination concurrently but separately, or administration of the individual agents of the combination sequentially by any suitable route. The dosage of the individual therapeutic agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

Combinations as reported herein may include embodiments wherein one or more of Compound 1 and an EGFR inhibitor are administered as a pharmaceutically acceptable salt or as a free base. There is no requirement that both compounds be administered as the same pharmaceutically acceptable salt, but they may be. In particular embodiments combinations comprise a free base form of Compound 1 and an EGFR inhibitor. In other embodiments combinations comprise an HCl form of Compound 1 and an EGFR inhibitor.

"Pharmaceutically acceptable salt" as used herein refers to acid addition salts or base addition salts of the compounds in the present disclosure. A pharmaceutically acceptable salt is any salt which retains the activity of the parent compound and does not impart any unduly deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like.

Embodiments may be hydrochloride salts. Pharmaceutically acceptable salts may be derived from amino acids including, but not limited to, cysteine. Methods for producing compounds as salts are known to those of skill in the art (see, e.g., Stahl et al., Handbook of Pharmaceutical Salts: Properties, Selection, and Use, Wiley-VCH; Verlag Helvetica Chimica Acta, Zurich, 2002; Berge et al., J. Pharm. Sci. 66: 1, 1977).

An "effective amount" of a combination of therapeutic agents (e.g., Compound 1 and an EGFR inhibitor) is an amount sufficient to provide an observable therapeutic benefit compared to HCC or IHCC left untreated in a subject or patient.

Active agents as reported herein can be combined with a pharmaceutically acceptable carrier to provide pharmaceutical formulations thereof. The particular choice of carrier and formulation will depend upon the particular route of administration for which the composition is intended.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, sorbic acid, potassium sorbate, partial glyceride mixtures of saturated vegetable fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene glycol and wool fat.

The compositions of the present invention may be suitable for parenteral, oral, inhalation spray, topical, rectal, nasal, buccal, vaginal or implanted reservoir administration, etc. In some embodiments, the formulation comprises ingredients that are from natural or non-natural sources. In some embodiments, the formulation or carrier may be provided in a sterile form. Non-limiting examples of a sterile carrier include endotoxin-free water or pyrogen-free water.

The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds are administered intravenously, orally, subcutaneously, or via intramuscular administration. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids and their glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents that are commonly used in the manufacture of pharmaceutically acceptable solid, liquid, or other dosage forms may also be used for the purposes of formulation.

For oral administration, a compound or salt may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with emulsifying and suspending agents. If desired, certain sweetening, flavoring or coloring agents may also be added. In addition preservatives may also be added. Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the drug within approximately 30 minutes after commencement of dissolution in a dissolution test.

"Sustained-release" or "extended-release" includes dosage forms whose drug-release characteristics of time course and/or location are chosen to accomplish therapeutic or convenience objectives not offered by conventional dosage forms such as a solution or an immediate release dosage form.

The term "steady-state" means that a plasma level for a given active agent or combination of active agents, has been achieved and which is maintained with subsequent doses of the active agent(s) at a level which is at or above the minimum effective therapeutic level and is below the minimum toxic plasma level for a given active agent(s).

The term "single formulation" as used herein refers to a single carrier or vehicle formulated to deliver effective amounts of both therapeutic agents to a patient. The single vehicle is designed to deliver an effective amount of each of the agents along with any pharmaceutically acceptable carriers or excipients. In some embodiments, the vehicle is a tablet, capsule, pill, or a patch.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents (Compound 1 or an EGFR inhibitor) along with pharmaceutically acceptable carriers and excipients. In some embodiments, the unit dose is one or more tablets, capsules, pills, or patches administered to the patient at the same time.

The term "dose range" as used herein refers to an upper and a lower limit of an acceptable variation of the amount of agent specified. Typically, a dose of an agent in any amount within the specified range can be administered to patients undergoing treatment.

The term "treat" is used herein to mean to relieve, reduce or alleviate at least one symptom of a disease in a subject. For example, in relation to HCC, the term "treat" may mean to arrest, delay the onset (i.e., the period prior to clinical manifestation of a disease or symptom of a disease) and/or reduce the risk of developing or worsening a symptom of a disease. The term "protect" is used herein to mean prevent delay or treat, or all, as appropriate, development or continuance or aggravation of symptoms of the disease in a subject.

The term "subject" or "patient" is intended to include animals, which are capable of suffering from or afflicted with HCC or IHCC. Examples of subjects or patients include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from HCC or IHCC.

The term "about" or "approximately" usually means within 20%, more preferably within 10%, and most preferably still within 5% of a given value or range. Alternatively, especially in biological systems, the term "about" means within about a log (i.e., an order of magnitude) preferably within a factor of two of a given value.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The term "synergistic effect" as used herein, refers to action of two agents such as, for example, Compound 1 and gefitinib, producing an effect, for example, reducing cell viability and/or cell proliferation or slowing the progression of HCC, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

In some embodiments, treatment is provided to a subject having hepatocellular carcinoma with altered FGFR4 and/or FGF19 (fibroblast growth factor 19) status.

In some embodiments, treatment may include or be performed in conjunction with analyzing FGFR4 and/or FGF19 status in a biological sample containing cells of said hepatocellular carcinoma, and if said hepatocellular carcinoma exhibits an FGFR4 and/or FGF19 alteration, treating a subject with a treatment effective amount of a therapeutic combination as described herein.

Methods of Treatment

Provided herein is a combination therapy useful for reducing the viability and/or proliferation of one or more cells. Such a combination may be useful for the treatment of HCC or IHCC. As discussed below, combinations provided herein may have a number of advantages.

One advantage of the combination disclosed herein is the unexpected synergistic effect of a combination of Compound 1 and an EGFR inhibitor on: (1) the reduction in the viability and/or proliferation of one or more cells; and (2) tumor growth inhibition and treatment of HCC or IHCC.

In some embodiments, provided herein is a single pharmaceutical formulation containing a combination of Compound 1 and an EGFR inhibitor. An advantage provided herein is the synergistic effect that results in the reduction of the viability and/or proliferation of a cell or in the treatment of HCC compared to treatment with a single dose of either drug. When the drugs are provided in a single unit dose or single formulation, the "pill burden" on a patient suffering from HCC is not increased.

As specified above, in one aspect, provided herein is a drug combination useful for treating, preventing, arresting, delaying the onset of and/or reducing the risk of developing, or reversing HCC in a mammal comprising administering to said mammal a combination therapy, comprising an effective amount of Compound 1 and an effective amount of an EGFR inhibitor.

In some embodiments, the subject to be treated (e.g., patient) is determined to be non-responsive or resistant to one or more HCC therapies, e.g., Compound 1. In other embodiments, the individual to be treated is responsive to Compound 1 therapy, but the therapy was improved with the administration of an EGFR inhibitor. For example, the patient is administered Compound 1 (e.g., 50 mg to 600 mg per day, 200 mg to 400 mg per day, or 300 mg per day for some period of time, e.g., more than one day, more than two days, more than three days, more than one week, more than one month, etc. After that time, an EGFR inhibitor could be administered to that patient in combination with Compound 1.

Amounts of EGFR inhibitor may vary depending on the EGFR inhibitor that is used. For example, gefitinib may be administered in an amount of 250 mg/day or 500 mg/day; afatinib may be administered at 10-50 mg/day, at 20-40 mg/day, at 20 mg/day, at 30 mg/day, or at 40 mg/day; and lapatinib may be administered at 100 mg/day to 1500 mg/day, at 1250 mg/day to 4500 mg/day, at 1500 mg/day to 5500 mg/day, at 500 mg/day, at 750 mg/day, at 1000 mg/day, at 1250 mg/day, and at 1500 mg/day. The daily dosage may be part of a cyclic regimen lasting 14 to 21 days or longer. The daily dosage amount may be administered as a single dosage or as multiple dosages.

One skilled in the art appreciates that the effective dose of the active drug may be lower than the actual amount administered. As such, provided herein are doses necessary to achieve a therapeutic dose.

In various embodiments, provided herein are methods that may be useful for treating HCC by administering an effective amount of Compound 1 and an EGFR inhibitor, to an individual having HCC. The amount of the combination of agents may be effective to treat the HCC. In one embodiment, the combination of agents has a synergistic effect. In one embodiment, even though one or more of the agents administered alone at a particular dosage may be effective, when administered in combination, at the same dosage of each agent, the treatment is more effective. For example, in one embodiment a combination of Compound 1 and gefitinib is more effective than is administration of either agent alone. In another embodiment a combination of Compound 1 and afatinib is more effective than is administration of either agent alone. In another embodiment a combination of Compound 1 and lapatinib is more effective than is administration of either agent alone.

Dosages

The optimal dose of the combination of agents for treatment of HCC can be determined empirically for each individual using known methods and will depend upon a variety of factors, including the activity of the agents; the age, body weight, general health, gender and diet of the individual; the time and route of administration; and other medications the individual is taking. Optimal dosages may be established using routine testing and procedures that are well known in the art.

For the combination therapy of the instant invention, the daily dose of Compound 1 is in the range of 50 mg to 600 mg. In some embodiments, the daily dose of Compound 1 is up to 600 mg. In certain embodiments, the daily dose of Compound 1 is up to 400 mg. In various embodiments, the daily dose of Compound 1 is up to 300 mg. In certain embodiments, the daily dose of Compound 1 is 200 mg to 400 mg. In one embodiment, the daily dose is 300 mg.

The time of administration can be chosen such that both the drugs are administered simultaneously, separately or sequentially, either in the morning or at night. Alternatively, one drug can be administered in the morning and the other at night. In certain embodiments, both the drugs can be administered as a single tablet, capsule, pill, patch or jelly formulation, once daily, either in the morning or at night.

The amount of combination of agents that may be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Pharmaceutical Formulations and Routes of Administration

Provided herein are pharmaceutical formulations comprising a combination of agents for reducing cell viability and/or cell proliferation. Such formulations may be useful for the treatment of HCC. The pharmaceutical formulations may additionally comprise a carrier or excipient, stabilizer, flavoring agent, and/or coloring agent.

A combination of agents may be administered using a variety of routes of administration known to those skilled in the art. Routes of administration include oral administration. In certain embodiments, a pharmaceutical formulation comprising a combination of agents may be taken orally in the form of liquid, syrup, tablet, capsule, powder, sprinkle, chewtab, or dissolvable disk. Alternatively, pharmaceutical formulations of the present invention can be administered intravenously or transdermally. Additional routes of administration are known to those skilled in the art (see, e.g., Remington's Pharmaceutical Sciences, Gennaro A. R., Ed., 20.sup.th Edition, Mack Publishing Co., Easton, Pa.).

In some embodiments, the Compound 1 and EGFR inhibitor are formulated as a paste, jelly, or suspension. For example, the drugs are dissolved, entrapped or suspended in the form of drug particles, microencapsulated particles, or drug-polymer particles in a gelatinous solution or semi-solid. An advantage of an oral jelly formulation is that it is easier to administer the drugs to patients who have difficulty swallowing tablets, capsules or pills. In certain embodiments, both agents are thoroughly mixed and suspended in an appropriate medium to form a paste or a gel. Additional agents can optionally be mixed to provide flavor during oral administration. Peanut butter or alginate, flavored with raspberry and a sweetener are examples of the many suitable taste masking agents. In various embodiments, the paste or jelly can also be formulated with suitable binders or excipients known in the art for topical administration.

Methods of preparing sustained release formulations in the Rum of tablets, capsules or pills are known in the art. In some embodiments, the sustained release formulation is prepared by coating the active ingredient of the drug with a polymer, preferably a water-insoluble polymer. For example, a water-insoluble polymer used in the pharmaceutical field as a sustained release coating agent, an enteric coating agent, or a gastric coating agent. The water-insoluble polymer can include, for example, ethyl cellulose, purified shellac, white shellac, aminoalkyl methacrylate copolymer RS, hydroxypropyl methylcellulose phthalate, hydroxypropyl methylcellulose acetate succinate, carboxymethylethylcellulose, cellulose acetate phthalate, methacrylic acid copolymer L, methacrylic acid copolymer LD, methacrylic acid copolymer S, aminoalkyl methacrylate copolymer E, or polyvinyl acetal diethylaminoacetate.

The type, degree of substitution and molecular weight of the water-insoluble polymers can depend on solubility of the active ingredient in water or an alcohol, the desired sustained release level and the like. The water-insoluble polymers can be used either alone or in combination. There can be further incorporated a hydrogenated oil, stearic acid, or cetanol as a coating auxiliary agent, and a middle-chain triglyceride, triacetin, triethyl citrate, or cetanol as a plasticizer.

In some embodiments, the sustained release formulation is a matrix-type tablet or granule. The active ingredient can be coated with up to 3 different types of polymers. These three different types of polymers can include: 1) a water insoluble polymer, such as ethylcellulose; 2) a pH independent gelling polymer, such as hydroxypropyl methylcellulose; and 3) a pH dependent gelling polymer, such as sodium alginate. These three different types of polymers can be used together to attenuate the release rate of the drugs.

Dosage Forms: Release Properties

Sustained-release formulations can achieve a degree of sustained effect. However, the exposure and/or the bioavailability of the active ingredient may vary based on a variety of factors, such as for example, the absorption window, the carriers or excipients used in the formulation, the mode of delivery of the formulation, and/or the transit time of the active ingredient through the gastrointestinal tract of the patient.

A combination therapy can contain at least one sustained-release portion for performing a sustained-release function and one immediate release portion for performing an immediate release function. In certain embodiments, when the combination therapy is in a single dosage form, it can be in the form of tablets formed from a mixture of sustained-release granules constituting a sustained-release portion and immediate-release granules constituting an immediate-release portion, a capsule preparation obtained by filling a capsule with sustained-release granules and immediate-release granules, or press-coated tablets in which an outer layer constituting an immediate-release portion is formed on an inner core constituting a sustained-release portion. There is, however, no limitation to the above embodiments.

Moreover, there are no particular limitations on the state of containment of each drug in the composition or in an immediate-release portion or a sustained-release portion; the Compound 1 may be dispersed uniformly in the composition, immediate release portion or sustained release portion, or may be contained in only one part of the composition, immediate-release portion or sustained-release portion, or may be contained such that there is a concentration gradient.

A sustained-release portion in the composition according to the present invention can contain at least one non-pH-dependent polymeric substance or pH-dependent polymeric substance for controlling drug release.

A non-pH-dependent polymeric substance used herein can comprise a polymeric substance whose charge state hardly changes under pH conditions generally found in the gastrointestinal tract, specifically from pH 1 to pH 8. This means, for example, a polymeric substance that does not have functional groups whose charge state changes depending on the pH such as basic functional groups such as amino groups or acidic functional groups such as carboxylic acid groups. Note that the non-pH-dependent polymeric substance can be included for giving the composition according to the present invention a sustained-release function, but may also be included for another purpose. Moreover, the non-pH-dependent polymeric substance used in the present invention may be water-insoluble, or may swell in water or dissolve in water to form a gel.

Examples of water-insoluble non-pH-dependent polymeric substances include, but are not limited to, cellulose ethers, cellulose esters, and methacrylic acid-acrylic acid copolymers (trade name Eudragit, manufactured by Rohm GmbH & Co. KG, Darmstadt, Germany). Examples include, but are not limited to, cellulose alkyl ethers such as ethylcellulose (trade name Ethocel, manufactured by Dow Chemical Company, USA), ethyl methylcellulose, ethyl propylcellulose or isopropylcellulose, and butylcellulose, cellulose aralkyl ethers such as benzyl cellulose, cellulose cyanoalkyl ethers such as cyanoethylcellulose, cellulose organic acid esters such as cellulose acetate butyrate, cellulose acetate, cellulose propionate or cellulose butyrate, and cellulose acetate propionate, ethyl acrylate-methyl methacrylate copolymers (trade name Eudragit NE, manufactured by Rohm GmbH & Co. KG, Darmstadt, Germany), and aminoalkyl methacrylate copolymer RS (trade names Eudragit RL, Eudragit RS). There are no particular limitations on the mean particle diameter of a water-insoluble polymer used in the present invention, but usually the lower this mean particle diameter the better the performance, with the mean particle diameter preferably being from 0.1 to 100 μm, more preferably from 1 to 50 μm, particularly preferably from 3 to 15 μm, most preferably from 5 to 15 μm. Moreover, examples of water-soluble or water-swelling non-pH-dependent polymeric substances include, but are not limited to, polyethylene oxide (trade name Polyox, manufactured by Dow Chemical Company, molecular weight 100,000 to 7,000,000), low-substituted hydroxypropyl cellulose (trade name L-HPC, manufactured by Shin-Etsu Chemical, Japan), hydroxypropyl cellulose (trade name HPC, manufactured by Nippon Soda, Co., Ltd, Japan), hydroxypropyl methylcellulose (trade names Metolose 60SH, 65SH, 90SH, manufactured by Shin-Etsu Chemical, Japan), and methylcellulose (trade name Metolose SM, manufactured by Shin-Etsu Chemical, Japan).

In some embodiments a single non-pH-dependent polymeric substance may be contained in the composition, or a plurality of the non-pH-dependent polymeric substances may be contained. The non-pH-dependent polymeric substance, if used in embodiments reported herein, may be a water-insoluble polymeric substance, more preferably ethylcellulose, an ethyl acrylate-methyl methacrylate copolymer (trade name Eudragit NE), or an aminoalkyl methacrylate copolymer RS (trade name Eudragit RL, Eudragit RS). Particularly preferable is at least one of ethylcellulose and an aminoalkyl methacrylate copolymer RS. Most preferable is ethylcellulose. There are no particular limitations on the amount of the non-pH-dependent polymeric substance contained in the composition; this amount can be adjusted as appropriate in accordance with the purpose such as controlling sustained drug release.

A pH-dependent polymeric substance that can be used in embodiments reported herein may be a polymeric substance whose charge state changes under pH conditions generally found in the gastrointestinal tract, specifically from pH 1 to pH 8. This means, for example, a polymeric substance having functional groups whose charge state changes depending on the pH such as basic functional groups such as amino groups or acidic functional groups such as carboxylic acid groups. The pH-dependent functional groups of the pH-dependent polymeric substance are preferably acidic functional groups, with the pH-dependent polymeric substance most preferably having carboxylic acid groups.

A pH-dependent polymeric substance used in the present invention may be water-insoluble, or may swell in water or dissolve in water to form a gel. Examples of pH-dependent polymeric substances used in the present invention include, but are not limited to, enteric polymeric substances. Examples of enteric polymeric substances include, but are not limited to, methacrylic acid-methyl methacrylate copolymers (Eudragit L100, Eudragit S100, manufactured by Rohm GmbH & Co. KG, Darmstadt, Germany), methacrylic acid-ethyl acrylate copolymers (Eudragit L100-55, Eudragit L30D-55, manufactured by Rohm GmbH & Co. KG, Darmstadt, Germany), hydroxypropyl methylcellulose phthalate (HP-55, HP-50, manufactured by Shin-Etsu Chemical, Japan), hydroxypropyl methylcellulose acetate succinate (AQOAT, manufactured by Shin-Etsu Chemical, Japan), carboxymethyl ethylcellulose (CMEC, manufactured by Freund Corporation, Japan), and cellulose acetate phthalate.

Examples of pH-dependent polymeric substances that swell in water or dissolve in water to form a gel include, but are not limited to, alginic acid, pectin, carboxyvinyl polymer, and carboxymethyl cellulose. In the present invention, a single pH-dependent polymeric substance may be contained in the composition, or a plurality of pH-dependent polymeric substances may be contained. The pH-dependent polymeric substance used in the present invention is preferably an enteric polymeric substance, more preferably a methacrylic acid-ethyl acrylate copolymer, a methacrylic acid-methyl methacrylate copolymer, hydroxypropyl methylcellulose phthalate, or hydroxypropyl methylcellulose acetate succinate, particularly preferably a methacrylic acid-ethyl acrylate copolymer.

When using a pH-dependent polymeric substance in the manufacturing process of a composition according to the present invention, a commercially available product of a powder type or a granular type, or a suspension type in which the pH-dependent polymeric substance has been dispersed in a solvent in advance can be used as is, or such a commercially available product can be used dispersed in water or an organic solvent. The lower the particle diameter of the pH-dependent polymeric substance the better the performance, with the pH-dependent polymeric substance preferably being of the powder type. In the case of a methacrylic acid-ethyl acrylate copolymer, an example is Eudragit L100-55. There are no particular limitations on the mean particle diameter of a pH-dependent polymeric substance used in the present invention, but the mean particle diameter is preferably from 0.05 to 100 μm, more preferably from 0.05 to 70 μm, most preferably from 0.05 to 50 μm. Moreover, there are no particular limitations on the amount of the pH-dependent polymeric substance, for example, in the case of an enteric polymeric substance, the amount is generally from 0.1 to 90 parts by weight, preferably from 1 to 70 parts by weight, more preferably from 5 to 60 parts by weight, particularly preferably from 10 to 50 parts by weight, based on 100 parts by weight of the composition.

A combination therapy according to embodiments reported herein may further contain any of various additives, such as any of various pharmacologically acceptable carriers such as diluents, lubricants, binders and disintegrants, as well as preservatives, colorants, sweeteners, plasticizers, film coating agents and so on, as necessary. Examples of diluents include, but are not limited to, lactose, mannitol, dibasic calcium phosphate, starch, pregelatinized starch, crystalline cellulose, light silicic anhydride, synthetic aluminum silicate, magnesium aluminate metasilicate or the like. Examples of lubricants include, but are not limited to, magnesium stearate, calcium stearate, talc, sodium stearyl fumarate or the like. Examples of binders include, but are not limited to, hydroxypropyl cellulose, methylcellulose, sodium carboxymethyl cellulose, hydroxypropyl methylcellulose, polyvinylpyrrolidone or the like. Examples of disintegrants include, but are not limited to, carboxymethyl cellulose, calcium carboxymethyl cellulose, croscarmellose sodium, sodium carboxymethyl starch, low-substituted hydroxypropyl cellulose or the like. Examples of preservatives include, but are not limited to, paraoxybenzoic acid esters, chlorobutanol, benzyl alcohol, phenethyl alcohol, dehydroacetic acid, sorbic acid or the like. Preferable examples of colorants include, but are not limited to, water-insoluble lake pigments, natural pigments (e.g., .beta.-carotene, chlorophyll, red ferric oxide), yellow ferric oxide, red ferric oxide, black ferric oxide or the like. Preferable examples of sweeteners include, but are not limited to, sodium saccharin, dipotassium glycyrrhizate, aspartame, stevia or the like. Examples of plasticizers include, but are not limited to, glycerol fatty acid esters, triethyl citrate, propylene glycol, polyethylene glycol or the like. Examples of film coating agents include, but are not limited to, hydroxypropyl methylcellulose, hydroxypropyl cellulose or the like.

Manufacturing Methods

To manufacture embodiments as reported herein, a single conventional method, or a combination of conventional methods, can be used. For example, when manufacturing drug-containing granules as a sustained-release portion or an immediate-release portion, granulation is the main operation, but this may be combined with other operations such as mixing, drying, sieving, and classification. As the granulation method, for example, a wet granulation method in which a binder and a solvent are added to the powder and granulation is carried out, a dry granulation method in which the powder is compressed and granulation is carried out, a molten granulation method in which a binder that melts on heating is added and heating and granulation are carried out, or the like can be used.

Furthermore, in accordance with the granulation method, an operating method such as a mixing granulation method using a planetary mixer, a screw mixer or the like, a high-speed mixing granulation method using a Henschel mixer, a Super mixer or the like, an extruding granulation method using a cylindrical granulator, a rotary granulator, a screw extruding granulator, a pellet mill type granulator or the like, a wet high-shear granulation method, a fluidized-bed granulation method, a compression granulation method, a crushing granulation method, or a spraying granulation method can be used. After the granulation, drying using a dryer, a fluidized bed or the like, cracking, and sieving can be carried out to obtain the granules or fine granules for use. Moreover, a granulation solvent may be used when preparing the composition according to the present invention. There are no particular limitations on such a granulation solvent, which may be water or any of various organic solvents, for example, water, a lower alcohol such as methanol or ethanol, a ketone such as acetone or methyl ethyl ketone, methylene chloride, or a mixture thereof.

For sustained-release granules contained in embodiments, at least one drug and at least one selected from non-pH-dependent polymeric substances and pH-dependent polymeric substances are mixed together, a diluent and a binder are added as necessary, and granulation is carried out to obtain granular matter. The granular matter obtained is dried using a tray dryer, a fluidized bed dryer or the like, and sieving is carried out using a mill or an oscillator, whereby the sustained-release granules can be obtained. Alternatively, as a method of manufacturing sustained-release granules in the present invention, it is possible to add at least one drug, at least one selected from non-pH-dependent polymeric substances and pH-dependent polymeric substances, and as necessary a diluent and a binder using a dry compactor such as a roller compactor or a slug tabletting machine, and carry out compression-molding while mixing, and then carry out granulation by cracking down to a suitable size. The granular matter prepared using such a granulator may be used as is as granules or fine granules according to the present invention, or may be further cracked using a power mill, a roll granulator, a rotor speed mill or the like, and sieved to obtain sustained-release granules. Note that immediate-release granules can also be manufactured as for the sustained-release granules.

A compression-molded product can be manufactured as a drug-containing sustained-release portion or immediate-release portion, or as a composition reported herein using a single conventional method, or a combination of conventional methods. For example, at least one drug, at least one selected from non-pH-dependent polymeric substances and pH-dependent polymeric substances, a diluent such as mannitol or lactose, a binder such as polyvinylpyrrolidone or crystalline cellulose, a disintegrant such as carmellose sodium or crospovidone, and a lubricant such as magnesium stearate or talc are used, and tabletting is carried out using an ordinary method, whereby the compression-molded product can be obtained. In this case, tabletting is the main operation in the method of manufacturing the compression-molded product, but this may be combined with other operations such as mixing, drying, sugar coating formation, and coating.

Examples of the method for the tabletting include, but are not limited to, direct compression molding in which at least one drug and pharmacologically acceptable additives are mixed together and then the mixture is directly compression-molded into tablets using a tabletting machine, and dry granule compression or wet granule compression in which sustained-release granules or immediate-release granules according to the present invention are subjected to compression-molding after adding a lubricant or a disintegrant as necessary. There are no particular limitations on the tabletting machine used in the compression molding; for example, a single-punch tabletting machine, a rotary tabletting machine, or a press-coated tabletting machine can be used.

Drug-containing sustained-release granules or immediate-release granules, or compression-molded product according to embodiments herein can be used as is in the form of granules or a tablet as the composition, but may also be subjected to further processing to manufacture the composition. For example, the compression-molded product or granules can be given a film coating using a film base material such as ethylcellulose, casein, methylcellulose, hydroxypropyl methylcellulose, methacrylic acid copolymer L, cellulose acetate phthalate, shellac or the like, or given a sugar coating using a sugar coating liquid containing saccharose, sugar alcohol, gum arabic powder, talc or the like, thus producing film-coated tablets or sugar-coated tablets. One solvent in this coating technique may be purified water, but an organic solvent such as an alcohol, a ketone, an ether or a chlorinated hydrocarbon, or a mixture thereof can also be used. For example, ethanol, acetone, methylene chloride or the like can be used as an organic solvent. Moreover, as the coating apparatus, an apparatus ordinarily used in coating techniques for manufacturing medicines can be used, with examples including a spray coating apparatus in which the coating is carried out by spraying a coating liquid or the like, and a rotor fluidized bed granulator for layering.

In the case of manufacturing capsule preparations, capsule preparations can be manufactured by filling sustained-release granules or immediate-release granules as above, or mini-tablets into hard gelatin capsules or HPMC capsules using an automatic capsule filling machine. Alternatively, in the case of the preparations for per-tube administration or a dry syrup that is used mixed with water or the like when taken, sustained-release granules or immediate-release granules as above can be mixed with a thickener or a dispersant so as to disperse these granules, the mixture then being made into granules or tablets. Furthermore, a liquid or jelly can be made using water, and substances selected from dispersants, emulsifiers, thickeners, preservatives, pH adjustors, sweeteners, flavorings, fragrances and so on. However, with respect to other manufacturing methods, there are no limitations to the above.

In order that embodiments described herein may be more fully understood, the following examples are set forth. It should be understood that these examples are for illustrative purposes only and are not to be construed as limiting.

EXAMPLES

Materials and Methods
Compounds and Drugs

Compound 1 is a selective, orally bioavailable small molecule FGFR4 inhibitor that is being developed by H3 Biomedicine. Gefitinib, afatinib, lapatinib, and cetuximab are FDA-approved EGFR inhibitors.

Cell Lines Tested

The cell line used, Hep3B (also called HEP3B.1-7), was sourced from American Type Culture Collection (ATCC), verified free of mycobacterium contamination and verified for identity by short tandem repeat analysis of 9 markers.

Cell Line Maintenance and Study Conditions

Medium conditions for growth included Eagle's Minimum Essential Medium (EMEM) (ATCC® 30-2003™) supplemented with 10% Fetal Bovine Serum (FBS) or RPMI1640 medium containing 10% FBS. Cells were maintained prior to and during experiments at 37° C., 5% $CO_2$, and at 95% relative humidity. Cell passage number was limited to between 12 and 20. During in vitro experiments cells were seeded at appropriate densities to provide logarithmic growth during and at least 24 hours beyond the experiment target compound exposure duration.

Compound Preparation and Presentation to Cells

Compounds for assay were serially diluted in dimethyl sulfoxide (DMSO) using a low-volume liquid handler (VIAFLO ASSIST and VIAFLO II electronic 16-channel pipette, 0.5-12.5 µL) in an 11-point half-log serial dilution to create a master dose response source (MDR) used for all tests. Antibody solutions were serially diluted in phosphate buffered saline (PBS).

Transfers of compounds and antibodies from the MDR source plates to cell ARP's were accomplished directly by low-energy acoustic transfer (ATS100, EDC) using combination-specific transfer maps (TransferTrack, BioSero). After transfer of compounds and antibodies to the assay plate, the dose-response range experienced by cells was typically 5 µM-50 pM and 30 nM-0.5 pM (5 logs), respectively. The final DMSO concentration in the assay was 0.1% for compound-compound combination, uniformly, and 0.05% for antibody-compound combinations, uniformly. Each assay plate was self-anchored containing duplicate 11×11 combination matrices, vehicle/DMSO or vehicle/PBS negative controls, cidal positive controls, and the static control agent cycloheximide.

Measurement of Anti-Proliferative Activity of Treated Cells

Cell proliferation assays were performed 72-144 h post-treatment using CellTiter-Glo® Luminescent Cell Viability Assay reagent (Promega) according to the manufacturer's instructions (CellTiter-Glo® Luminescent Cell Viability Assay Technical Bulletin Instructions for Use of Product(s) G7570, G7571, G7572, G7573 Literature #TB288, Revised 3/15), and then measuring the luminescent signal on a microtiter plate reader (Envision, PE).

Cell proliferation was evaluated using the time zero (T0) signal as the positive control and the within-plate vehicle wells (DMSO) as the negative control. Data was converted to percent inhibition and falls into the range from 0% to 100% of growth where 0% equals the signal at T0 and 100% equals uninhibited or maximal growth. Cell growth at or near 0% is considered a static response.

Cell viability or death was evaluated using the response data for within-plate cidal controls compounds (1 µM bortezomib, 1 µM staurosporine) and the T0 signal as the negative control. Data was converted to percent inhibition and falls into the range from −100% to 0%. Cell growth at or near −100% is considered a cidal response.

Determination of Compound Synergy In Vitro

Compound 1 and the EGFR inhibitors were tested as single-agents and in combinations against the Hep3B cell model. Relative percent inhibition data were calculated by data analysis software (ECABIA, H3 Biomedicine) as described, and then transformed into a 0-200% data format (200%=cidal, 100%=static, 0%=no effect) compatible with further analysis.

Combination effects were then assessed using Chalice software (Horizon Discovery) comparing combination responses to their matched single-agent effects using the Loewe Additivity Model (Lehar J et al 2009 and Zimmermann G R et al 2006). Drug concentration ranges where synergistic effects occurred can be visualized in Chalice by comparing the full Dose-matrix Chart to the Loewe Additivity Model Chart, and by direct observation of the Excess Response Chart. Quantitative assessment can be made within a study or across anchored studies by the area and intensity of the combination response which is provided by the Chalice synergy score. Self-cross experiments and tests with other additive-only combinations served as baseline controls.

Xenograft Generation, Dosing and Measurement of Antitumor Activity

The human hepatocellular cancer cell line Hep3B was cultured in RPMI1640 medium containing 10% fetal bovine serum at 37° C. in a 5% $CO_2$ atmosphere and kept in exponential growth phase. For harvesting, the cells were washed with phosphate buffered saline, incubated with 0.25% trypsin-EDTA, and suspended in a 1:1 mixture of RPMI1640 medium and Matrigel (Corning) at a final concentration of $5 \times 10^7$ cells/mL. To generate xenografts, 0.1-mL of the inoculum was injected subcutaneously into the right flank region of mice, giving a final concentration of $5 \times 10^6$ cells/mouse. When the mean tumor volume (TV) reached approximately 170 mm³ (10 days after implantation), 56 mice were selected based on their TVs, and were sorted into 7 treatment groups with 8 animals per group. Per os (PO) treatment with Compound 1 (100 and 300 mg/kg) alone or in combination with vehicle (control) or gefitinib (50, 100, 200 mg/kg) administered every 12 hours (BID) continued for 15 days. The administration volume (0.1 mL/10 g body weight) was calculated from the individual mouse body weight (BW) before administration. Body weights were measured daily and tumor measurements were performed twice weekly.

The TV in mm³ was calculated according to the following formula: TV=length×width²×0.5 length: largest diameter of tumor (mm) width: diameter perpendicular to length (mm) The Tumor Growth Inhibition % (TGI) was calculated according to the following formula:

$$\frac{\text{Average Control } TV \text{ Day } X - \text{Treatment } TV \text{ Day } X}{\text{Average Control } TV \text{ Day } X} \times 100$$

where Day X is any day of measurement.

The anti-tumor effects of the treatment, Partial (PR) and complete regression (CR), stable (SD) and progressive (PD) disease were defined by the H3 Xenograft Model Response Criteria (Appendix 4). Mice with >20% body weight loss compared to their Day 1 body weight or bearing tumors with the longest diameter>2000 mm were immediately euthanized to prevent any pain or suffering in the animal as according to IACUC guidelines defined by the H3 Biomedicine Animal Care and Use Program and study protocol 13-05-1 g.

Statistical Analysis

Data are expressed as the mean±SEM for TV or ±STDEV for BW. The differences in TV on Day 15 between the vehicle treated and Compound 1 combination treated groups were analyzed by two way ANOVA followed by Dunnett's post hoc test. The relative body weight changes were analyzed by two way ANOVA followed by Dunnett's post hoc. Statistical analyses were performed using the GraphPad Prism version 5.04 (GraphPad Software, La Jolla, Calif.).

H3 Xenograft Model Response Criteria

Progressive disease (PD): 3 consecutive measurements >120% of starting volume or 3 consecutive increasing measurements from best response, Stable disease (SD): 3 consecutive measurements >50% and <120% of starting volume, Partial regression (PR): 3 consecutive measurements <50% of starting volume, Complete regression (CR): 3 consecutive measurements <30 mm³.

Results

In Vitro Combination Studies

To determine whether FGFR4 and EGFR inhibitors synergize in reducing cell viability and/or proliferation, Compound 1 (an FGFR4 inhibitor) and four EGFR inhibitors, gefitinib, afatinib, lapatinib, and cetuximab were tested in combinations using HEP3B cell line in vitro (a representative HCC cell line). The cells were exposed to compounds and then the effect on viability was measured after 72 hours.

Compound 1 and Gefitinib

As single agents, the highest doses of 1 µM Compound 1 and 5 µM gefitinib reduced cell viability 72% and 43%, respectively (FIG. 1A) whereas the combination of 1 µM Compound 1 and 5 µM gefitinib led to total cell killing (i e. 200% effect). In addition, lower doses of Compound 1 and gefitinib when combined, reduced cell viability to a greater extent compared to the corresponding single-agent doses (FIG. 1A). Excess inhibition over additivity was calculated using the Loewe Additivity Model and synergistic values were observed starting from 0.01 µM Compound 1 and 0.05 µM gefitinib (FIG. 1B).

Figure 1B:
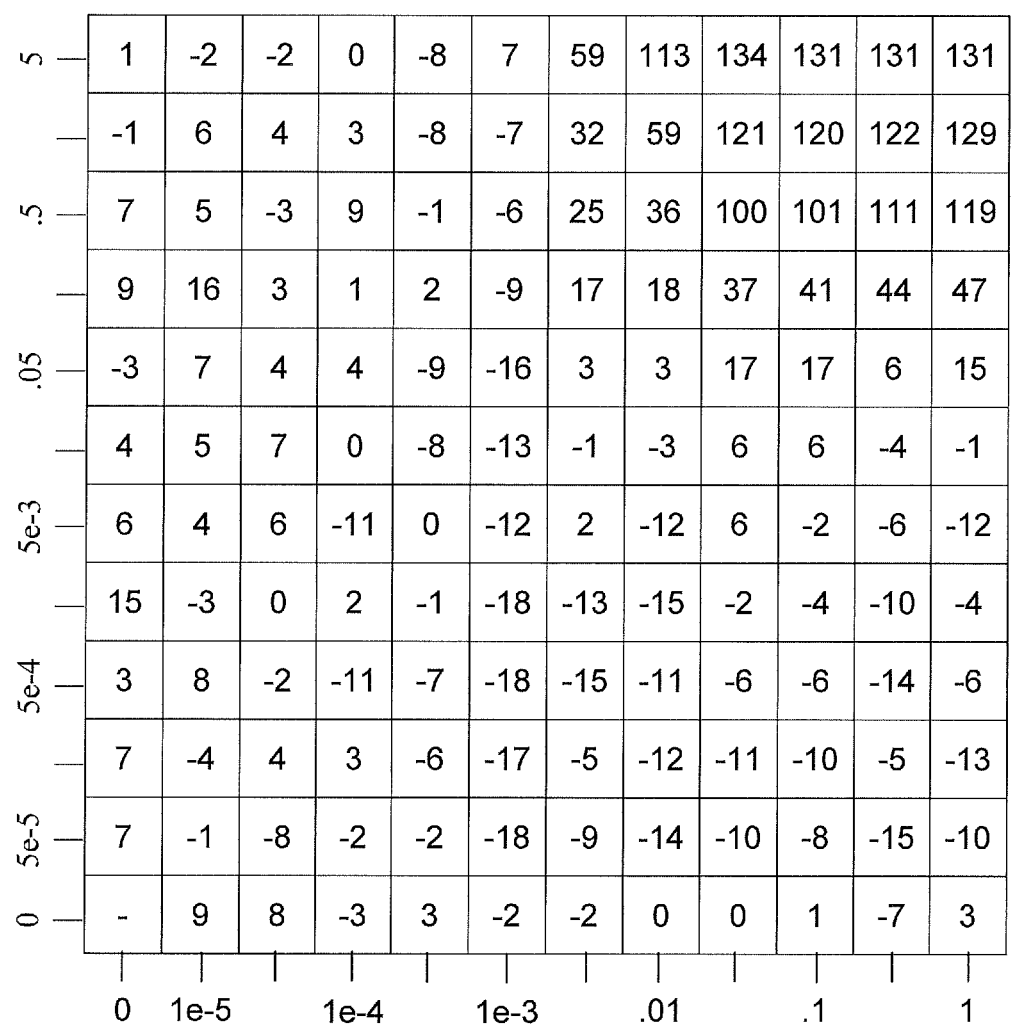
FIG. 1B shows excess inhibition over Loewe additivity for Compound 1 and gefitinib.

FIG. 1A and FIG. 1B show that Compound 1 and gefitinib synergistically inhibit growth of HEP3B cells in vitro. HEP3B cells were treated for 72 hours with different doses of Compound 1 and gefitinib. Inhibition of cell viability was measured using CellTiter-Glo (FIG. 1A), and Chalice software was used to calculate excess inhibition over Loewe additivity for each Compound 1 and gefitinib dose combination (FIG. 1B).

Compound 1 and Afatinib

Figure 2A:
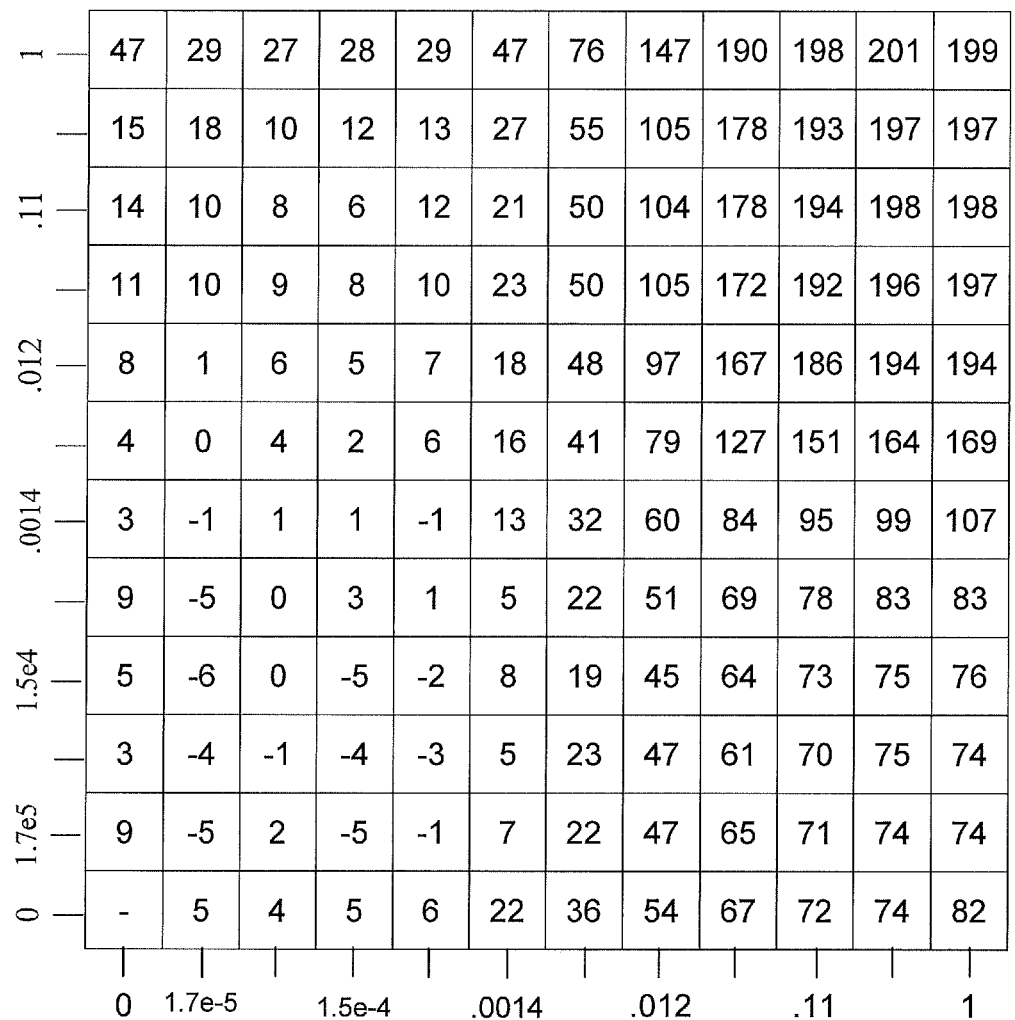
FIG. 2A shows inhibition of cell viability as measured by CellTiter-Glo for Compound 1 and afatinib.

As single-agents, the highest doses of 1 µM Compound 1 and 1 µM afatinib reduced cell viability 82% and 47%, respectively (FIG. 2A) whereas the combination of 1 µM Compound 1 and 1 µM afatinib led to total cell killing (i.e. 200% effect). In addition, lower doses of Compound 1 and afatinib when combined, reduced cell viability to a greater extent compared to the corresponding single agent doses (FIG. 2A). Excess inhibition over additivity was calculated using the Loewe additivity model and synergistic values were observed starting from 0.12 µM Compound 1 and 0.004 µM afatinib (FIG. 2B).

Figure 2B:
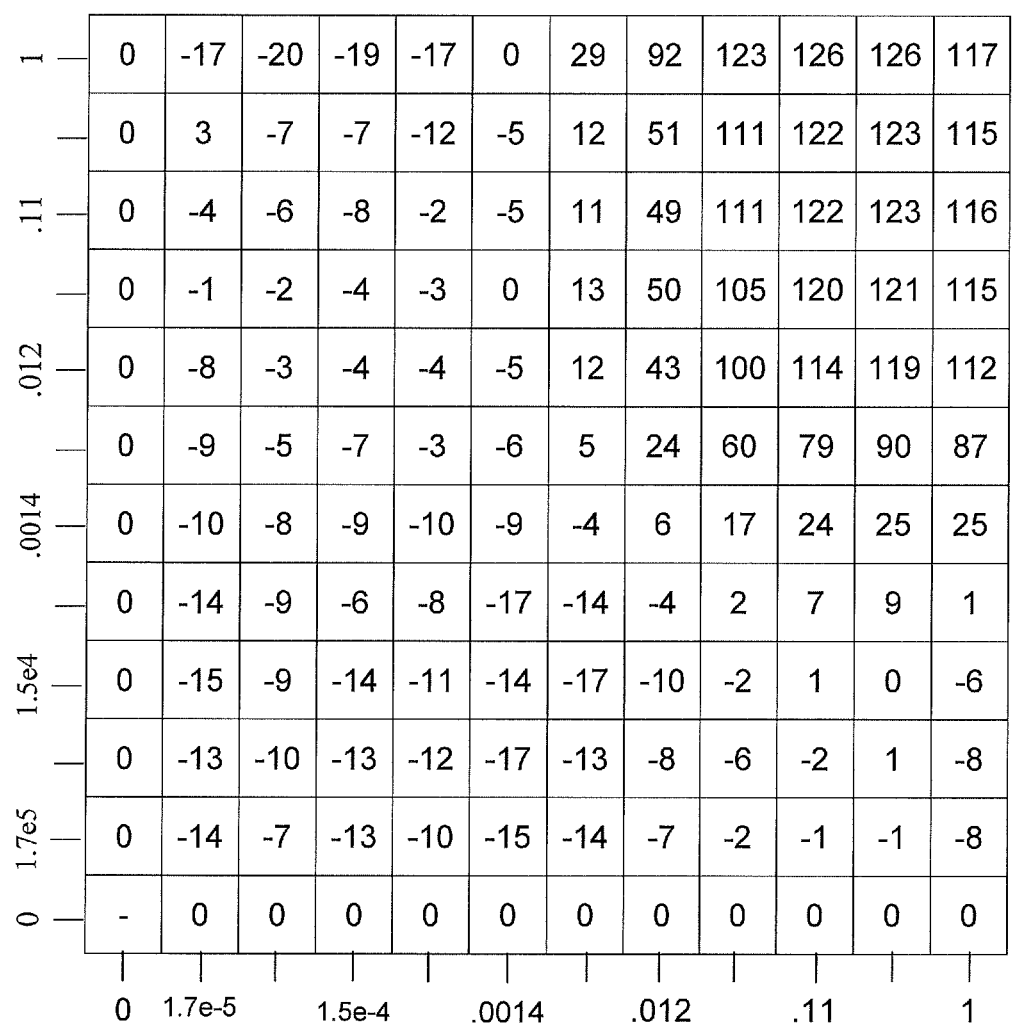
FIG. 2B shows excess inhibition over Loewe additivity for Compound 1 and afatinib.

FIG. 2A and FIG. 2B show Compound 1 and afatinib synergistically inhibit growth of HEP3B cells in vitro. HEP3B cells were treated for 72 hours with different doses of Compound 1 and afatinib. Inhibition of cell viability was measured using CellTiter-Glo (FIG. 2A), and Chalice software was used to calculate excess inhibition over Loewe additivity for each Compound 1 and afatinib dose combination (FIG. 2B).

Compound 1 and Lapatinib

Figure 3A:
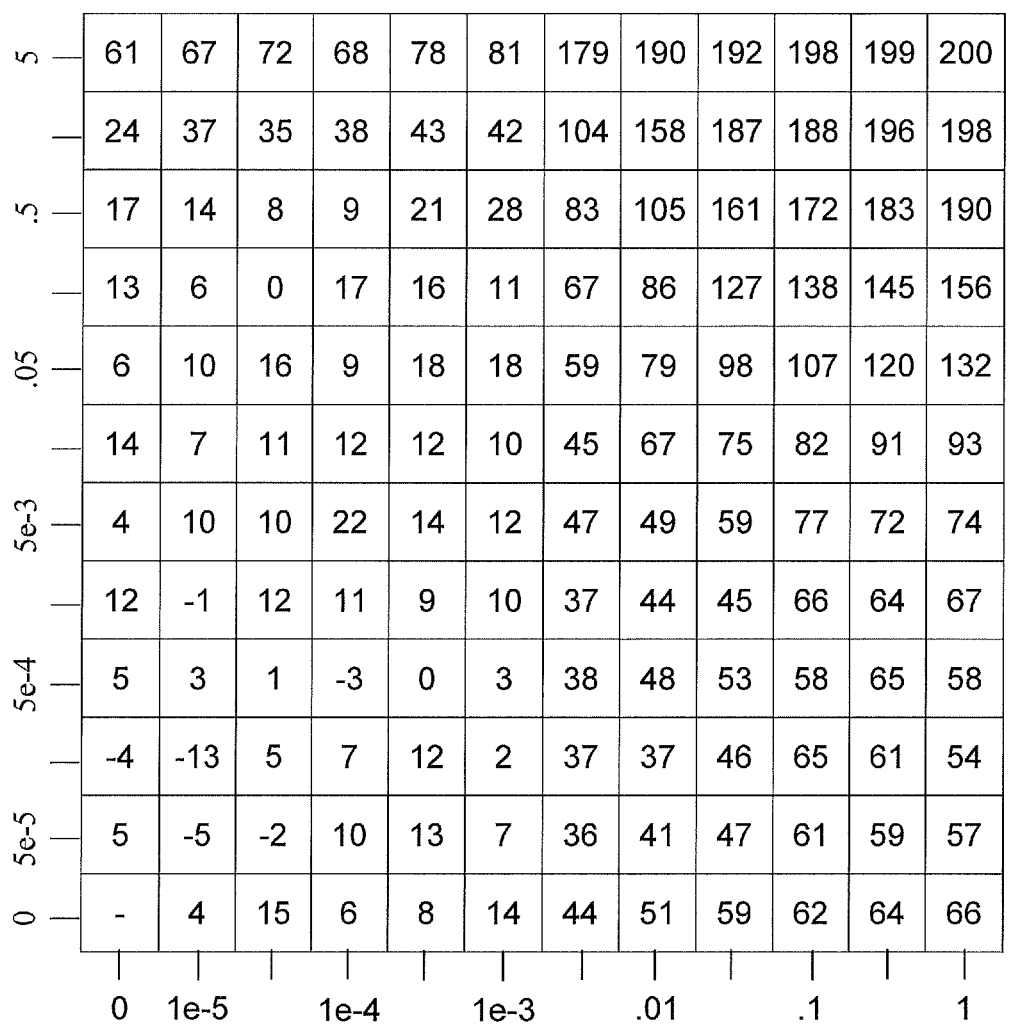
FIG. 3A shows inhibition of cell viability as measured by CellTiter-Glo for Compound 1 and lapatinib.

As single agents, the highest doses of 1 µM Compound 1 and 5 µM lapatinib reduced cell viability 66% and 61%, respectively (FIG. 3A) whereas the combination of 1 µM Compound 1 and 5 µM lapatinib led to total cell killing (i.e. 200% effect). In addition, lower doses of Compound 1 and lapatinib when combined, reduced cell viability to a greater extent compared to the corresponding single agent doses (FIG. 3A). Excess inhibition over additivity was calculated using the Loewe additivity model and synergistic values were observed starting from 0.001 µM Compound 1 and 0.005 µM lapatinib (FIG. 3B).

Figure 3B:
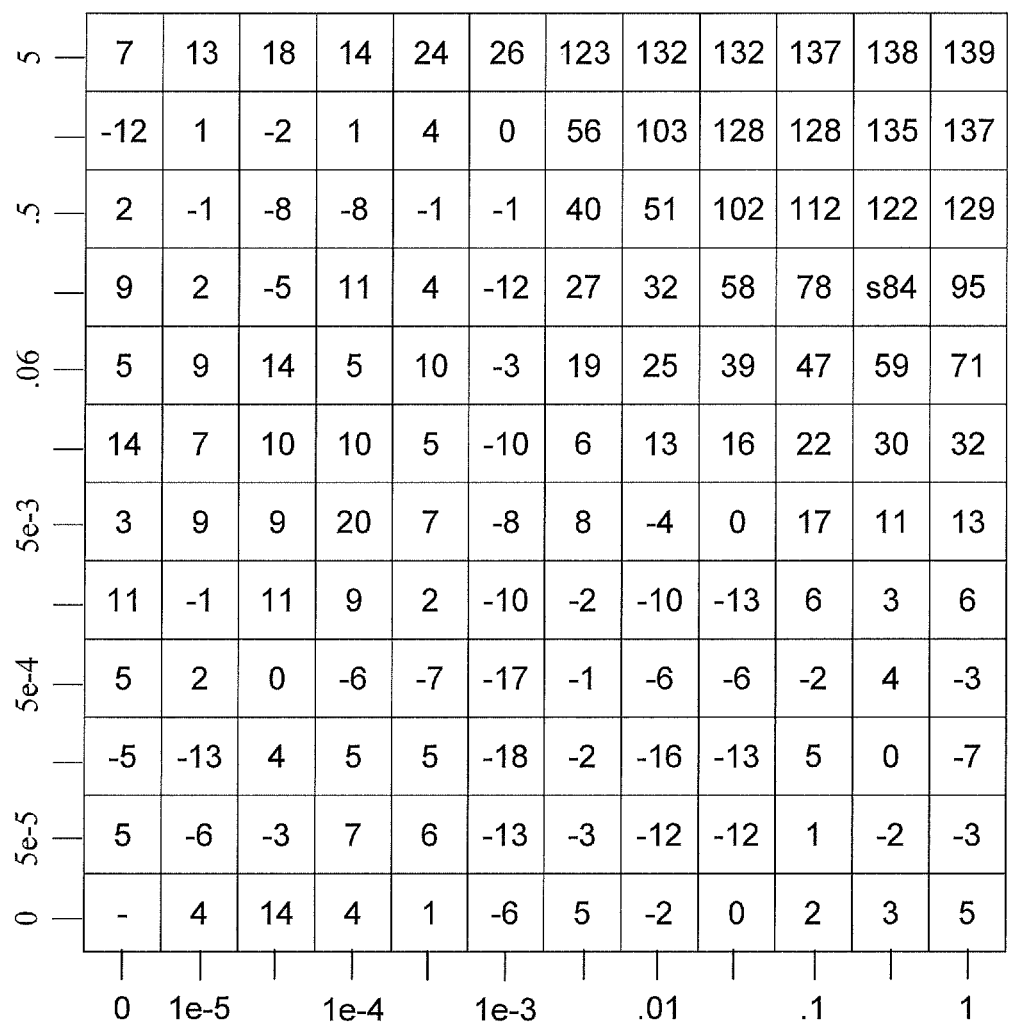
FIG. 3B shows excess inhibition over Loewe additivity for Compound 1 and lapatinib.

FIG. 3A and FIG. 3B shows Compound 1 and lapatinib synergistically inhibit growth of HEP3B cells in vitro. HEP3B cells were treated for 72 hours with different doses of Compound 1 and lapatinib. Inhibition of cell viability was measured using CellTiter-Glo (FIG. 3A), and Chalice software was used to calculate excess inhibition over Loewe additivity for each Compound 1 and lapatinib dose combination (FIG. 3B).

Compound 1 and Cetuximab

Figure 4A:
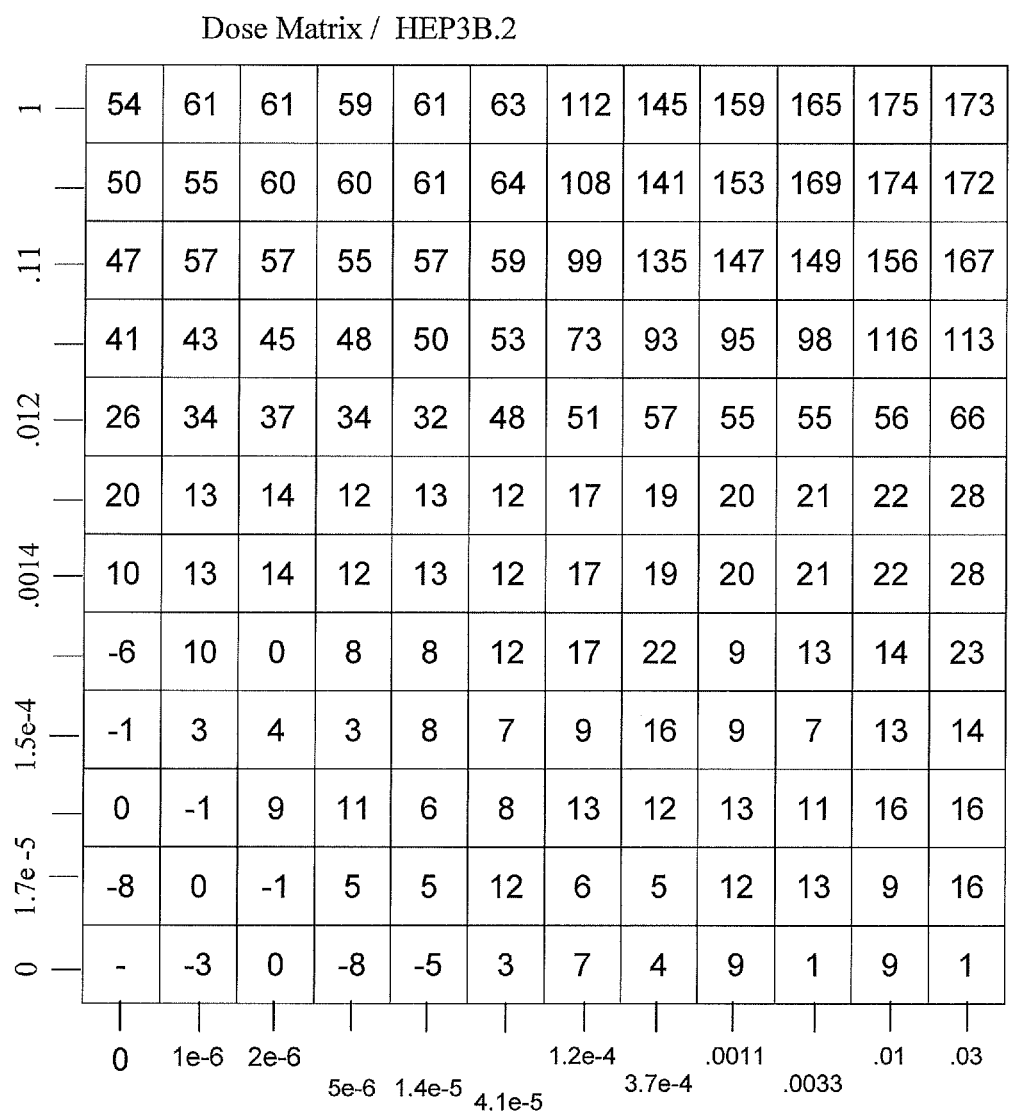
FIG. 4A and FIG. 4B show Compound 1 and cetuximab synergistically inhibit growth of HEP3B cells in vitro.

As single agents, the highest doses of 1 µM Compound 1 and 30 nM cetuximab reduced cell viability 46% and 1%, respectively (FIG. 4A) whereas the combination of 1 µM Compound 1 and 30 nM cetuximab reduced viability greatly (173% effect). In addition, lower doses of Compound 1 and cetuximab when combined, reduced cell viability to a greater extent compared to the corresponding single agent doses (FIG. 4A). Excess inhibition over additivity was calculated using the Loewe additivity model and synergistic values were observed starting from 0.001 µM Compound 1 and 0.00004 µM cetuximab (FIG. 4B).

Figure 4B:
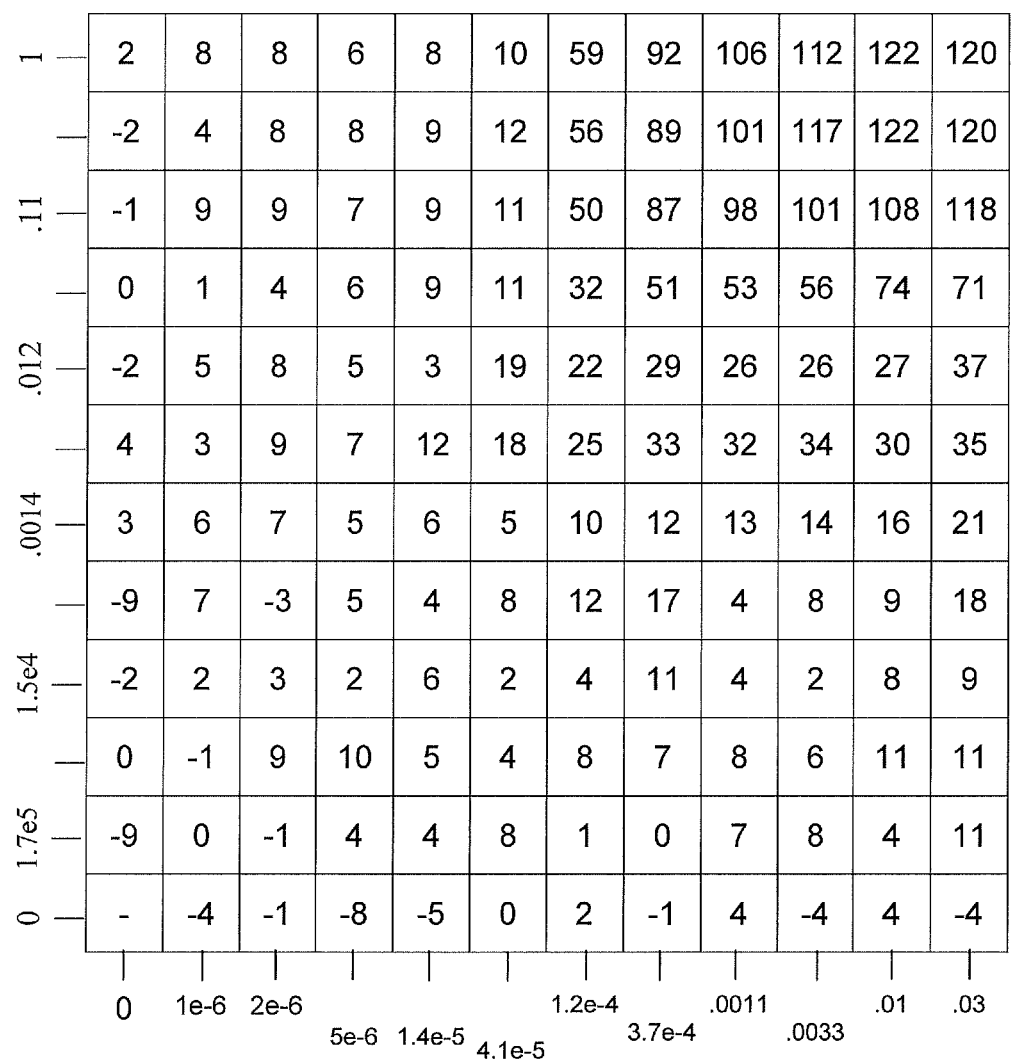

FIG. 4A and FIG. 4B show Compound 1 and cetuximab synergistically inhibit growth of HEP3B cells in vitro. HEP3B cells were treated for 72 hours with different doses of Compound 1 and cetuximab. Inhibition of cell viability was measured using CellTiter-Glo (FIG. 4A), and Chalice software was used to calculate excess inhibition over Loewe additivity for each Compound 1 and cetuximab dose combination (FIG. 4B).

In Vivo Combination Studies

Figure 5A:
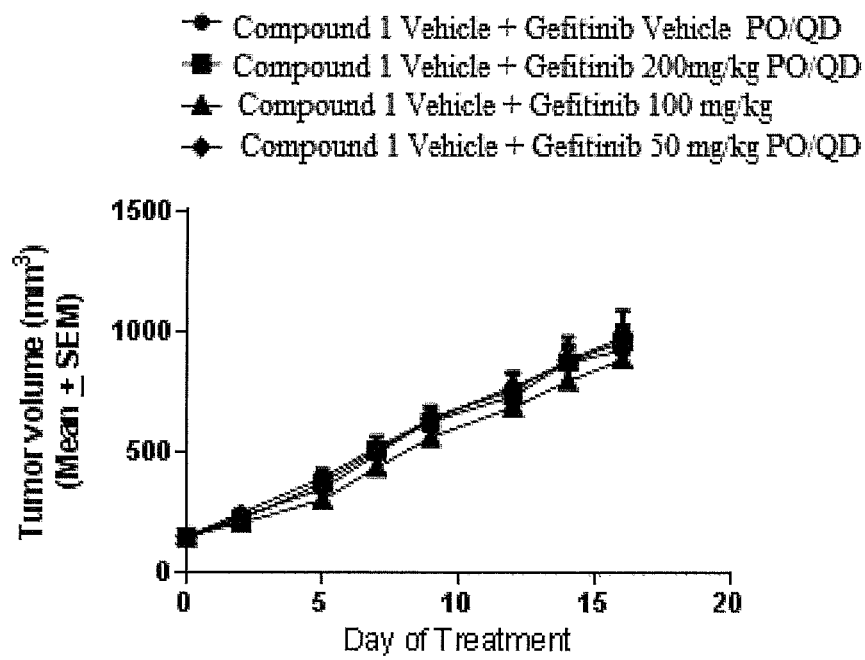
FIG. 5A shows tumor volume for gefitinib as a single agent.

To determine whether Compound 1 and gefitinib synergistically affect the tumor growth in vivo, the HEP3B cell line was grown as a xenograft in female nude immunocompromised mice. Tumor-bearing mice were treated daily for 17 days with 100 mg/kg or 300 mg/kg Compound 1, and 50, 100, or 200 mg/kg gefitinib as single agents or in combination. Gefitinib as single agent did not inhibit tumor growth at any dose level (FIG. 5A). In contrast, Compound 1 single agent resulted in Tumor Growth Inhibition (TGI) of 16% at 100 mg/kg and 64% at 300 mg/kg ($p<0.05$ for 300 mg/kg Compound 1 compared to vehicle control, FIG. 5B and FIG. 5C).

The combination of 100 mg/kg Compound 1 and gefitinib resulted in significant enhancement of the antitumor effects with all 3 dose levels in comparison to the Compound 1 100 mg/kg single agent with TGI of 27% for 50 mg/kg (8/8 PD), 32% for 100 mg/kg (8/8 PD) and, 72% for 200 mg/kg (3/8 SD and 5/8 PD; $p<0.05$ for all dose combinations using 100 mg/kg Compound 1 compared to vehicle control). The combination of 300 mg/kg Compound 1 and gefitinib also resulted in significant enhancement of the antitumor effects with all 3 dose levels in comparison to the Compound 1 300 mg/kg single agent with TGI of 75% for 50 mg/kg (2/8 SD and 6/8 PD), 89% for 100 mg/kg (3/8 PR, 4/8 SD and 1/8 PD), and 98% for 200 mg/kg (5/8 CR, 2/8 PR, and 1/8 SD; $p<0.05$ for all dose combinations for 300 mg/kg Compound 1 compared to vehicle control). None of the treatments resulted in any toxicities as measured by body weight or observations of pre-clinical health conditions (data not shown).

Figure 5B:
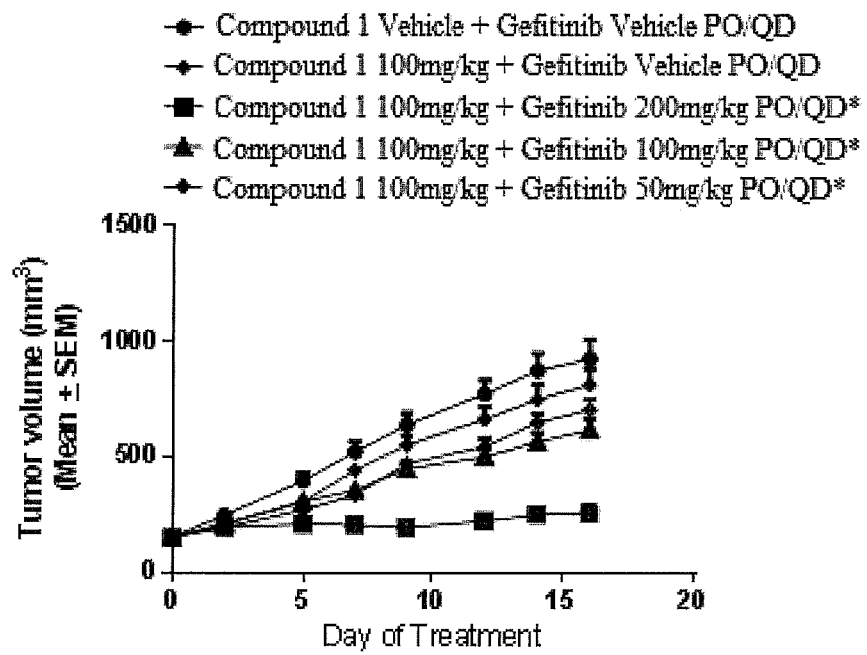
FIG. 5B and FIG. 5C show tumor volume for combinations of gefitinib and Compound 1.
Figure 5C:
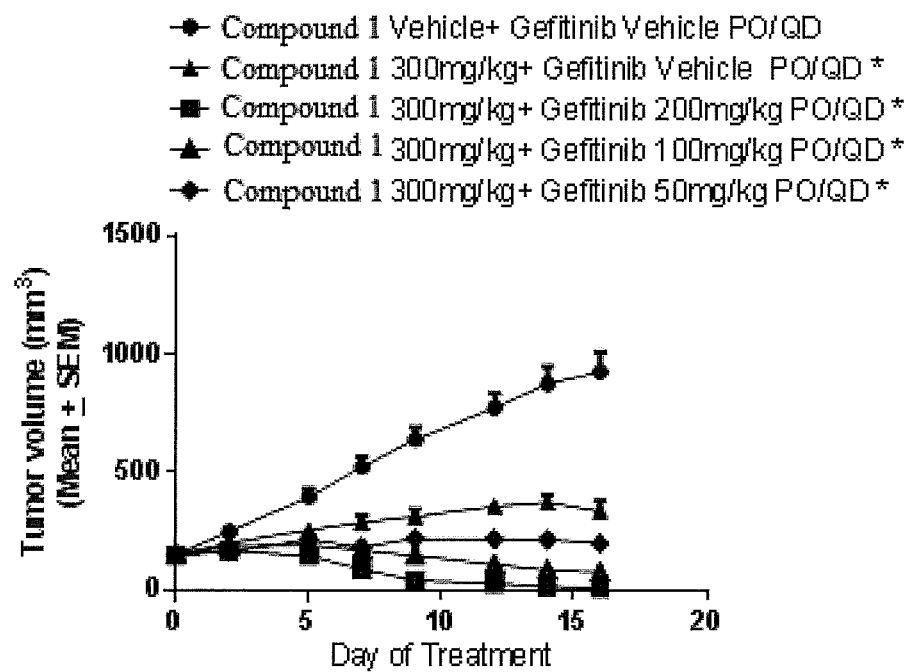

FIG. 5A, FIG. 5B, and FIG. 5C show antitumor effects of oral Compound 1 and gefitinib in the Hep3B xenograft model of hepatocellular carcinoma. Both Compound 1 and gefitinib was given orally (PO) once daily (QD) for 17 days. Data represent the mean±SEM (Tumor Volume). FIG. 5A shows gefitinib as single agent. FIG. 5B shows three doses of gefitinib with 100 mg/kg N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof (*$p<0.05$ at the 100 mg/kg Compound 1 dose in combination with 200 mg/kg gefitinib compared to 100 mg/kg Compound 1 single agent using two way ANOVA followed by Dunnett's post hoc test). FIG. 5C shows three doses of gefitinib with 300 mg/kg Compound 1 (*$p<0.05$ at the 300 mg/kg dose of Compound 1 in combination with 100 or 200 mg/kg gefitinib compared to 300 mg/kg Compound 1 using two way ANOVA followed by Dunnett's post hoc test).

We claim:

1. A method of treating hepatocellular carcinoma in a patient in need thereof, comprising administering to the patient a combination of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and an EGFR inhibitor or a pharmaceutically acceptable salt thereof, wherein said combination synergistically inhibits growth of hepatocellular carcinoma cells.

2. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 50 mg to 600 mg.

3. The method of claim 2, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage between 200 mg to 400 mg.

4. The method of claim 3, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof is administered in a daily dosage of 300 mg.

5. The method of claim 1, wherein the EGFR inhibitor is selected from the group consisting of 4-quinazolinamine N-(3-chloro-4-fluorophenyl)-7-methoxy-6-[3-(4-morpholinyl)propoxy]), (gefitinib), N-[4-[(3-Chloro-4-fluorophenyl)amino]-7-[[(3S)-tetrahydro-3-furanyl]oxy]-6-quinazolinyl]-4(dimethylamino)-2-butenamide) (afatinib), N-(3-chloro-4-{[(3-fluorophenyl)methyl]oxy}phenyl)-6-[5-({[2-(methylsulfonyl)ethyl]amino}methyl)-2-furanyl]-4-quinazolinamine bis(4-methylbenzenesulfonate) monohydrate (lapatinib), and cetuximab.

6. The method of claim 5, wherein the EGFR inhibitor is gefitinib.

7. The method of claim 6, wherein the gefitinib is administered in a daily dosage of 250 mg.

8. The method of claim 6, wherein the combination synergistically inhibits growth of hepatocellular carcinoma cells in a range of 17-134 as quantified by Loewe additivity equation.

9. The method of claim 8, wherein the combination synergistically inhibits growth of hepatocellular carcinoma cells in a range of 36-134 as quantified by Loewe additivity equation.

10. The method of claim 9, wherein the combination synergistically inhibits growth of hepatocellular carcinoma cells in a range of 59-134 as quantified by Loewe additivity equation.

11. The method of claim 10, wherein the combination synergistically inhibits growth of hepatocellular carcinoma cells in a range of 100-134 as quantified by Loewe additivity equation.

12. The method of claim 5, wherein the EGFR inhibitor is afatinib.

13. The method of claim 12, wherein the afatinib is administered in a daily dosage of 20 mg/day.

14. The method of claim 12, wherein the afatinib is administered in a daily dosage of 30 mg/day.

15. The method of claim 12, wherein the afatinib is administered in a daily dosage of 40 mg/day.

16. The method of claim 5, wherein the EGFR inhibitor is lapatinib.

17. The method of claim 16, wherein the lapatinib is administered in a daily dosage of between 1000 mg to 1500 mg.

18. The method of claim 17, wherein the lapatinib is administered in a daily dosage of 1000 mg.

19. The method of claim 17, wherein the lapatinib is administered in a daily dosage of 1250 mg.

20. The method of claim 17, wherein the lapatinib is administered in a daily dosage of 1500 mg.

21. The method of claim 5, wherein the EGFR inhibitor is cetuximab.

22. The method of claim 21, wherein the cetuximab is administered in a weekly dosage of between 200-300 mg/m$^2$.

23. The method of claim 22, wherein the cetuximab is administered in a weekly dosage of 250 mg/m$^2$.

24. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered as separate formulations.

25. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered as a single formulation.

26. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered sequentially.

27. The method of claim 1, wherein the N-(2-((6-(3-(2,6-dichloro-3,5-dimethoxyphenyl)-1-methylureido)pyrimidin-4-yl)amino)-5-(4-ethylpiperazin-1-yl)phenyl)acrylamide or a pharmaceutically acceptable salt thereof and the EGFR inhibitor are administered simultaneously.

28. The method of claim 1, comprising the free base form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide.

29. The method of claim 1, wherein the pharmaceutically acceptable salt of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide is a hydrochloride salt form of N-(2-((6-(3-(2,6-dichloro-3,5-dimethoxyphenyl)-1-methylureido)pyrimidin-4-yl)amino)-5-(4-ethylpiperazin-1-yl)phenyl)acrylamide.

* * * * *